United States Patent
Rufini et al.

(10) Patent No.: US 10,426,775 B2
(45) Date of Patent: Oct. 1, 2019

(54) METHODS FOR TREATING FRIEDREICH'S ATAXIA WITH ETRAVIRINE

(71) Applicant: Fratagene Therapeutics srl, Rome (IT)

(72) Inventors: Alessandra Rufini, Rome (IT); Giulia Alfedi, Rome (IT); Roberto Testi, Rome (IT)

(73) Assignee: FRATAGENE THERAPEUTICS SRL, Rome (IT)

( * ) Notice: Subject to any disclaimer, the term of this patent is extended or adjusted under 35 U.S.C. 154(b) by 0 days.

(21) Appl. No.: 16/128,419

(22) Filed: Sep. 11, 2018

(65) Prior Publication Data

US 2019/0076429 A1    Mar. 14, 2019

Related U.S. Application Data

(60) Provisional application No. 62/556,794, filed on Sep. 11, 2017.

(51) Int. Cl.
*A61K 31/506* (2006.01)
*A61P 25/02* (2006.01)

(52) U.S. Cl.
CPC ............ *A61K 31/506* (2013.01); *A61P 25/02* (2018.01)

(58) Field of Classification Search
CPC .................................................. A61K 31/506
See application file for complete search history.

(56) References Cited

U.S. PATENT DOCUMENTS

| | | | |
|---|---|---|---|
| 8,703,749 B2 | 4/2014 | Testi et al. | |
| 8,815,230 B2 | 8/2014 | Testi et al. | |
| 2006/0025445 A1 | 2/2006 | Xiang et al. | |
| 2007/0197649 A1 | 8/2007 | Munnich et al. | |
| 2012/0149909 A1 | 6/2012 | Castells Boliart et al. | |
| 2013/0109658 A1 | 5/2013 | Testi et al. | |
| 2017/0296540 A1 | 10/2017 | Testi et al. | |

FOREIGN PATENT DOCUMENTS

| | | |
|---|---|---|
| EP | 1 378 753 A1 | 1/2002 |
| WO | 2006050819 A1 | 5/2006 |
| WO | 2016/046759 A3 | 6/2011 |
| WO | 2012014083 A2 | 2/2012 |
| WO | 2012028961 A2 | 3/2012 |
| WO | 2012/149478 A2 | 11/2012 |
| WO | 2013/052613 A1 | 4/2013 |
| WO | 2016/046759 A2 | 3/2016 |
| WO | 2016103223 A1 | 6/2016 |

OTHER PUBLICATIONS

Gonzalez-Cabo P, Palau F. Mitochondrial pathophysiology in Friedreich's ataxia. J Neurochem 2013;126 Suppl 1:53-64.
Allavena C, Katlama C, Cotte L, et al. Long-term efficacy and safety of etravirine-containing regimens in a real-life cohort of treatment-experienced HIV-1-infected patients. Infect Dis (Lond) 2016;48(5):392-398.
Benini M, Fortuni S, Condo I, et al. E3 Ligase RNF126 Directly Ubiquitinates Frataxin, Promoting Its Degradation: Identification of a Potential Therapeutic Target for Friedreich Ataxia. Cell Rep 2017;18(8):2007-2017.
Berge et al. (1977) J. Pharm. Sci., 66, 1-19.
Bradley JL, Blake JC, Chamberlain S, Thomas PK, Cooper Jm, Schapira AH. Clinical, biochemical and molecular genetic correlations in Friedreich's ataxia. Hum Mol Genet 2000;9(2):275-282.
Bradley JL, Homayoun S, Hart PE, Schapira AH, Cooper JM. Role of oxidative damage in Friedreich's ataxia. Neurochem Res 2004;29(3):561-567.
Campuzano V, Montermini L, Lutz Y, et al. Frataxin is reduced in Friedreich ataxia patients and is associated with mitochondrial membranes. Hum Mol Genet 1997;6(11):1771-1780.
Campuzano V, Montermini L, Molto MD, et al. Friedreich's ataxia: autosomal recessive disease caused by an intronic GAA triplet repeat expansion. Science (New York, NY 1996;271(5254):1423-1427.
Chantrel-Groussard K, Geromel V, Puccio H, et al. Disabled early recruitment of antioxidant defenses in Friedreich's ataxia. Hum Mol Genet 2001;10(19):2061-2067.
Chutake YK, Lam CC, Costello WN, Anderson MP, Bidichandani SI. Reversal of epigenetic promoter silencing in Friedreich ataxia by a class I histone deacetylase inhibitor. Nucleic Acids Res 2016;44(11):5095-5104.
Codazzi F, Hu A, Rai M, et al. Friedreich ataxia-induced pluripotent stem cell-derived neurons show a cellular phenotype that is corrected by a benzamide HDAC inhibitor. Hum Mol Genet 2016;25(22):4847-4855.
Condò I, Malisan F, Guccini I, Serio D, Rufini A, Testi R. Molecular control of the cytosolic aconitase/IRP1 switch by extramitochondrial frataxin. Hum Mol Genet 2010;19(7):1221-1229.
Condò I, Ventura N, Malisan F, Rufini A, Tomassini B, Testi R. In vivo maturation of human frataxin. Hum Mol Genet 2007;16(13):1534-1540.
Condò, I., Ventura, N., Malisan, F., Tomassini, B. and Testi, R. A pool of extramitochondrial frataxin that promotes cell survival. J. Biol. Chem. 2006, 281, 16750-16756.
Das K, Clark AD, Jr., Lewi PJ, et al. Roles of conformational and positional adaptability in structure-based design of TMC125-R165335 (etravirine) and related non-nucleoside reverse transcriptase inhibitors that are highly potent and effective against wild-type and drug-resistant HIV-1 variants. Journal of medicinal chemistry 2004;47(10):2550-2560.
De Bethune MP. Non-nucleoside reverse transcriptase inhibitors (NNRTIs), their discovery, development, and use in the treatment of HIV-1 infection: a review of the last 20 years (1989-2009). Antiviral Res 2010;85(1):75-90.

(Continued)

Primary Examiner — James D. Anderson
(74) Attorney, Agent, or Firm — Kilpatrick Townsend & Stockton LLP

(57) ABSTRACT

The disclosure provides methods for the treatment of Friedreich's ataxia (FRDA), an autosomal recessive ataxia caused by mutation of the FXN gene, by administering to a subject a therapeutically effective amount of etravirine, or a pharmaceutically acceptable salt thereof. Etravirine is demonstrated to increase the levels of frataxin precursor and intermediate and mature forms of frataxin.

17 Claims, 6 Drawing Sheets

Specification includes a Sequence Listing.

(56) References Cited

OTHER PUBLICATIONS

De Biase I, Chutake YK, Rindler PM, Bidichandani SI. Epigenetic silencing in Friedreich ataxia is associated with depletion of CTCF (CCCTC-binding factor) and antisense transcription. PLoS One 2009;4(11):e7914.
Duraes F, Pinto M, Sousa E. Old Drugs as New Treatments for Neurodegenerative Diseases. Pharmaceuticals (Basel) 2018;11(2).
Durr A, Cossee M, Agid Y, et al. Clinical and genetic abnormalities in patients with Friedreich's ataxia. N Engl J Med 1996;335(16):1169-1175.
Eglen RM. Enzyme fragment complementation: a flexible high throughput screening assay technology. Assay and drug development technologies 2002;1(1 Pt 1):97-104.
Filla A, De Michele G, Cavalcanti F, et al. The relationship between trinucleotide (GAA) repeat length and clinical features in Friedreich ataxia. Am J Hum Genet 1996;59(3):554-560.
Guillemont J, Pasquier E, Palandjian P, et al. Synthesis of novel diarylpyrimidine analogues and their antiviral activity against human immunodeficiency virus type 1. Journal of medicinal chemistry 2005;48(6):2072-2079.
Harding AE. Friedreich's ataxia: a clinical and genetic study of 90 families with an analysis of early diagnostic criteria and intrafamilial clustering of clinical features. Brain 1981;104(3):589-620.
Katlama C, Clotet B, Mills A, et al. Efficacy and safety of etravirine at week 96 in treatment-experienced HIV type-1-infected patients in the DUET-1 and DUET-2 trials. Antivir Ther 2010;15(7):1045-1052.
Koeppen AH, Becker AB, Qian J, Feustel PJ. Friedreich Ataxia: Hypoplasia of Spinal Cord and Dorsal Root Ganglia. J Neuropathol Exp Neurol 2017;76(2):101-108.
Koeppen AH, Mazurkiewicz JE. Friedreich ataxia: neuropathology revised. J Neuropathol Exp Neurol 2013;72(2):78-90.
Koeppen AH, Morral JA, Davis An, et al. The dorsal root ganglion in Friedreich's ataxia. Acta Neuropathol 2009;118(6):763-776.
Koeppen AH, Ramirez RL, Becker AB, et al. The pathogenesis of cardiomyopathy in Friedreich ataxia. PLoS One 2015;10(3):e0116396.
Li L, Shen X, Liu Z, et al. Activation of Frataxin Protein Expression by Antisense Oligonucleotides Targeting the Mutant Expanded Repeat. Nucleic Acid Ther 2018;28(1):23-33.
Libri V, Yandim C, Athanasopoulos S, et al. Epigenetic and neurological effects and safety of high-dose nicotinamide in patients with Friedreich's ataxia: an exploratory, open-label, dose-escalation study. Lancet 2014.
Marmolino D. Friedreich's ataxia: past, present and future. Brain Res Rev 2011;67(1-2):311-330.
Mateo I, Llorca J, Volpini V, Corral J, Berciano J, Combarros O. GAA expansion size and age at onset of Friedreich's ataxia. Neurology 2003;61(2):274-275.
Nelson M, Hill A, van Delft Y, Moecklinghoff C. Etravirine as a Switching Option for Patients with HIV RNA Suppression: A Review of Recent Trials. AIDS Res Treat 2014;2014:636584.
Parkinson MH, Boesch S, Nachbauer W, Mariotti C, Giunti P. Clinical features of Friedreich's ataxia: classical and atypical phenotypes. J Neurochem 2013;126 Suppl 1:103-117.
Pastore A, Puccio H. Frataxin: a protein in search for a function. J Neurochem 2013;126 Suppl 1:43-52.
Paupe V, Dassa EP, Goncalves S, et al. Impaired nuclear Nrf2 translocation undermines the oxidative stress response in Friedreich ataxia. PLoS One 2009;4(1):e4253.
Rotig A, de Lonlay P, Chretien D, et al. Aconitase and mitochondrial iron-sulphur protein deficiency in Friedreich ataxia. Nat Genet 1997;17(2):215-217.
Rufini A, Cavallo F, Condo I, et al. Highly specific ubiquitin-competing molecules effectively promote frataxin accumulation and partially rescue the aconitase defect in Friedreich ataxia cells. Neurobiol Dis 2015;75:91-99.

Rufini A, Fortuni S, Arcuri G, et al. Preventing the ubiquitin-proteasome-dependent degradation of frataxin, the protein defective in Friedreich's ataxia. Hum Mol Genet 2011;20(7):1253-1261.
Sandeo S, Scott BD, McMackin MZ, et al. Dyclonine rescues frataxin deficiency in animal models and buccal cells of patients with Friedreich's ataxia. Hum Mol Genet 2014;23(25):6848-6862.
Santoro A, Anjomani Virmouni S, Paradies E, et al. Effect of diazoxide on Friedreich ataxia models. Hum Mol Genet 2018;27(6):992-1001.
Sardana D, Zhu C, Zhang M, Gudivada RC, Yang L, Jegga AG. Drug repositioning for orphan diseases. Brief Bioinform 2011;12(4):346-356.
Schulz JB, Dehmer T, Schols L, et al. Oxidative stress in patients with Friedreich ataxia. Neurology 2000;55(11):1719-1721.
Shameer K, Readhead B, Dudley JT. Computational and experimental advances in drug repositioning for accelerated therapeutic stratification. Curr Top Med Chem 2015;15(1):5-20.
Soragni E, Gottesfeld JM. Translating HDAC inhibitors in Friedreich's ataxia. Expert Opin Orphan Drugs 2016;4(9):961-970.
Soragni E, Miao W, Iudicello M, Jacoby D, De Mercanti S, Clerico M, Longo F, Piga A, Ku S, Campau E, Du J, Penalver P, Rai M, Madara JC, Nazor K, O'Connor M, Maximov A, Loring JF, Pandolfo M, Durelli L, Gottesfeld JM, Rusche JR. 2014. Epigenetic therapy for Friedreich ataxia. Ann Neurol 76:489-508.
Strawser C, Schadt K, Hauser L, et al. Pharmacological therapeutics in Friedreich ataxia: the present state. Expert review of neurotherapeutics 2017;17(9):895-907.
Tai G, Corben LA, Yiu EM, Milne SC, Delatycki MB. Progress in the treatment of Friedreich ataxia. Neurol Neurochir Pol 2018;52(2):129-139.
Tomassini B, Arcuri G, Fortuni S, et al. Interferon gamma upregulates frataxin and corrects the functional deficits in a Friedreich ataxia model. Hum Mol Genet 2012;21(13):2855-2861.
Treier M., Staszewski L.M., Bohmann D. Ubiquitin-dependent c-Jun degradation in vivo is mediated by the delta domain. Cell. 1994;78:787-798.
Usach I, Melis V, Pens JE. Non-nucleoside reverse transcriptase inhibitors: a review on pharmacokinetics, pharmacodynamics, safety and tolerability. J Int AIDS Soc 2013;16:1-14.
Ye H, Rouault TA. Human iron-sulfur cluster assembly, cellular iron homeostasis, and disease. Biochemistry 2010;49(24):4945-4956.
Acquaviva, F., et al. Extra-mitochondrial localisation of frataxin and its association with IscUI during enterocyte-like differentiation of the human colon adenocarcinoma cell line Caco-2. J Cell Sci 118, 3917-3924 (2005).
Adinolfi, S., et al. Bacterial frataxin Cya Y is the gatekeeper of iron-sulfur cluster formation catalyzed by IscS. Nat Struct Mal Biol 16, 390-396 (2009).
Al-Mandawi, S., Pinto, R.M., Ismail, O., Varshney, D., Lymperi, S., Sandi, C., Trabzuni, D., and Pook, M. (2008). The Friedreich ataxia GAA repeat expansion mutation induces comparable epigenetic changes in human and transgenic mouse brain and heart tissues. Hum Mol Genet 17, 735-746.
Balcer et al. ("Consensus clinical management guidelines for Friedreich ataxia." FARA. Nov. 2014. http://www.curefa.org/pdf/research/ClinicalManagementGuidelinesForFA(1).pdf. 209 pages).
Bedford, L., Lowe, J., Dick, L.R., Mayer, R.J., and Brownell, J.E., Ubiquitin-like protein conjugation and the ubiquitin-proteasome system as drug targets. Nature reviews Drug discovery 10, 29-46, (2011).
Bidichandani, S.I., Ashizawa, T., and Patel, P.I. (1998). The GAA triplet-repeat expansion in Friedreich ataxia interferes with transcription and may be associated with an unusual DNA structure. Am J Hum Genet 62, 111-121.
Boutet, S.C., Disatnik, M.H., Chan, L.S., Iori, K. & Rando, T.A. Regulation of Pax3 by proteasomal degradation of monoubiquitinated protein in skeletal muscle progenitors. Cell 130, 349-362 (2007).
Brady, G.P., Jr. & Stouten, P.F. Fast prediction and visualization of protein binding pockets with PASS. J Comput Aided Mol Des 14, 383-401 (2000).
Brownell, J.E., Sintchak, M.D., Gavin, J.M., Liao, H., Bruzzese, F.J., Bump, N.J., Soucy, T.A., Milhollen, M.A., Yang, X., Burkhardt, A.L., et al., Substrate-assisted inhibition of ubiquitin-like protein-

(56) References Cited

OTHER PUBLICATIONS activating enzymes: the NEDD8 E1 inhibitor MLN4924 forms a NEDD8-AMP mimetic in situ. Molecular cell 37, 102-111 (2010).
Bulteau, A.L., O'Neill, H.A., Kennedy, M.C., Ikeda-Saito, M., Isaya, G., and Szweda, L.I., Frataxin acts as an iron chaperone protein to modulate mitochondrial aconitase activity, Science 305, 242-245, (2004).
Chen, Q., Xie, W., Kuhn, D.J., Voorhees, P.M., Lopez-Girona, A., Mendy, D., Corral, L.G., Krenitsky, V.P., Xu, W., Moutouh-de Parseval, L. et al., Targeting the p27 E3 ligase SCF(Skp2) results in p27-and Skp2-mediated cell-cycle arrest and activation of autophagy, Blood 111, 4690-4699 (2008).
Cnop, M., Mulder, H., and Igoillo-Esteve, M. (2013). Diabetes in Friedreich ataxia. J Neurochem 126 Suppl 1, 94-102.
Delatycki, M.B. ("Evaluating the progression of Friedreich ataxia and its treatment." J Neurol 256 Suppl 1, 36-41 (2009)).
Deshaies, R.J. & Joazeiro, C.A. Ring domain E3 ubiquitin ligases. Annu Rev Biochem 78, 399-434 (2009).
Dhe-Paganon, S., Shigeta, R., Chi, Y.I., Ristow, M. & Shoelson, S.E., Crystal structure of human frataxin, J Biol Chem 275, 30753-30756 (2000).
Germain, D., Ubiquitin-dependent and -independent mitochondrial protein quality controls: implications in ageing and neurodegenerative diseases, *Mol Microbiol* 70, 1334-1341 (2008).
Glickman, M.H., and Ciechanover, A., The ubiquitin-proteasome proteolytic pathway: destruction for the sake of construction. Physiological reviews 82, 373-428 (2002).
Gottesfeld, J.M., Small molecules affecting transcription in Friedreich ataxia. Pharmacol Ther 116, 236-248 (2007).
Greene, E., Mahishi, L., Entezam, A., Kumari, D., and Usdin, K. (2007). Repeat-induced epigenetic changes in intron 1 of the frataxin gene and its consequences in Friedreich ataxia. Nucleic Acids Res 35, 3383-3390.
Habelhah, H. et al., Regulation of 2-oxoglutarate (alpha-ketoglutarate) dehydrogenase stability by the RING finger ubiquitin ligase Siah. *J Biol Chem* 279, 53782-53788 (2004).
He, Lingyan et al., Discovering Potent Inhibitors Against the β-Hydroxyacyl-Acyl Carrier Protein Dehydratase (FabZ) of Helicobacter pylori: Structure-Based Design, Synthesis, Bioassay, and Crystal Structure Determination; *J. Med. Chem.* 2009, 52(8), 2465-2481.
Herman, D., Jenssen, K., Burnett, R., Soragni, E., Perlman, S.L., and Gottesfeld, J.M., Histone deacetylase inhibitors reverse gene silencing in Friedreich's ataxia. Nat Chem Biol 2, 551-558 (2006).
Issaeva, N., Bozko, P., Enge, M., Protopopova, M., Verhoef, L.G., Masucci, M., Pramanik, A., and Selivanova, G., Small molecule RITA binds to p53, blocks p53-HDM-2 interaction and activates p53 function in tumors, Nature medicine 10, 1321-1328 (2004).
Iwai, K. & Tokunaga, F. Linear polyubiquitination: a new regulator of NF-kappaB activation. EMBO Rep 10, 706-713 (2009).
J. G. Cannon Chapter Nineteen in Burger's Medicinal Chemistry and Drug Discovery, Fifth Edition, vol. I: Principles and Practice, Wiley-I nterscience 1995, pp. 783-802.
Kisselev, A.F., van der Linden, W.A., and Overkleeft, H.S., Proteasome inhibitors: an expanding army attacking a unique target, Chemistry & biology 19, 99-115, (2012).
Komander, D., The emerging complexity of protein ubiquitination. *Biochem Soc Trans* 37, 937-953 (2009).
Koutnikova, H., Campuzano, V., and Koenig, M. (1998). Maturation of wild-type and mutated frataxin by the mitochondrial processing peptidase. Hum Mol Genet 7, 1485-1489.
Kravtsova-Ivantsiv, Y., Cohen, S. & Ciechanover, A. Modification by single ubiquitin moieties rather than polyubiquitination is sufficient for proteasomal processing of the p105 NF-kappaB precursor. Mol Cell 33, 496-504 (2009).
Kussie, P.H., Gorina, S., Marechal, V., Elenbaas, B., Moreau, J., Levine, A.J., and Pavletich, N.P., Structure of the MDM2 oncoprotein bound to the p53 tumor suppressor transactivation domain, Science 274, 948-953 (1996).

Li, W., et al. Genome-wide and functional annotation of human E3 ubiquitin ligases identifies MULAN, a mitochondrial E3 that regulates the organelle's dynamics and signaling. PLoS One 3, e1487 (2008).
Mariotti et al. ("Erythropoietin in Friedreich ataxia." International Society for Neurochemistry, J. Neurochem. (2013) 126 (Suppl. 1 ), 80-87).
Marmolino, D. & Acquaviva, F., Friedreich's Ataxia: from the (GAA)n repeat mediated silencing to new promising molecules for therapy. Cerebellum 8, 245-259 (2009).
Marmolino, D., Acquaviva, F., Pinelli, M., Monticelli, A., Castaldo, I., Filla, A., and Cocozza, S., PPAR-gamma agonist Azelaoyl PAF increases frataxin protein and mRNA expression: new implications for the Friedreich's ataxia therapy, Cerebellum 8, 98-103 (2009).
Martelli, A., and Puccio, H., Dysregulation of cellular iron metabolism in Friedreich ataxia: from primary iron-sulfur cluster deficit to mitochondrial iron accumulation, Front Pharmacol 5, 130 (2014).
Musco, G., et al., Towards a structural understanding of Friedreich's ataxia: the solution structure of frataxin, *Structure* 8, 695-707 (2000).
Pandolfo, M. & Pastore, A. The pathogenesis of Friedreich ataxia and the structure and function of frataxin. *J Neurol* 256 Suppl 1, 9-17 (2009).
Pandolfo, M., Friedreich ataxia: the clinical picture, J Neurol *256 Suppl 1*, 3-8 (2009).
Patani et al. (Chemical Reviews, 1996, vol. 96, No. 8).
Perdomini, M., Belbellaa, B., Monassier, L., Reutenauer, L., Messaddeq, N., Cartier, N., Crystal, R.G., Aubourg, P., and Puccio, H. (2014). Prevention and reversal of severe mitochondrial cardiomyopathy by gene therapy in a mouse model of Friedreich's ataxia. Nature medicine 20, 542-547.
Puccio, H., Multicellular models of Friedreich ataxia. *J Neurol* 256 Suppl 1, 18-24 (2009).
Rentsch, A., Landsberg, D., Brodmann, T., Bulow, L., Girbig, A.K., and Kalesse, M., Synthesis and pharmacology of proteasome inhibitors, Angewandte Chemie 52, 5450-5488 (2013).
Richardson et al., "Therapeutic strategies in Friedreich's Ataxia", Brain Res. Jun. 13, 2013; 1514: 91-97.
Richardson, P.G., Mitsiades, C., Hideshima, T., and Anderson, K.C., Bortezomib: proteasome inhibition as an effective anticancer therapy, Annu Rev Med 57, 33-47 (2006).
Richardson et al. ("Development of potential iron chelators for the treatment of Friedreich's ataxia: ligands that mobilize mitochondrial iron." Biochimica et Biophysica Acta 1536 (2001) 133-140).
Rotin, D. & Kumar, S. Physiological functions of the HECT family of ubiquitin ligases. Nat Rev Mol Cell Biol 10, 398-409 (2009).
Roxburgh, P., Hock, A.K., Dickens, M.P., Mezna, M., Fischer, P.M., and Vousden, K.H.Small molecules that bind the Mdm2 RING stabilize and activate p53, Carcinogenesis 33, 791-798, 2012.
Saeki, Y., et al. Lysine 63-linked polyubiquitin chain may serve as a targeting signal for the 26S proteasome. EMBO J 28, 359-371 (2009).
Sakamoto, N., Ohshima, K., Montermini, L., Pandolfo, M., and Wells, R.D. (2001). Sticky DNA, a self- associated complex formed at long GAA*TTC repeats in intron 1 of the frataxin gene, inhibits transcription. The Journal of biological chemistry 276, 27171-27177.
Schmucker, S., Argentini, M., Carelle-Calmels, N., Martelli, A. & Puccio, H. The in vivo mitochondrial two-step maturation of human frataxin. Hum Mal Genet 17, 3521-3531 (2008).
Schulz, J.B., Boesch, S., Burk, K., Durr, A., Giunti, P., Mariotti, C., Pousset, F., Schols, L., Vankan, P., and Pandolfo, M., Diagnosis and treatment of Friedreich ataxia: a European perspective. Nat Rev Neurol 5, 222-234 (2009).
Schwartz, A.L. & Ciechanover, A., Targeting proteins for destruction by the ubiquitin system: implications for human pathobiology, Annu Rev Pharmacol Toxicol 49, 73-96 (2009).
Shan, Y., Schoenfeld, R.A., Hayashi, G., Napoli, E., Akiyama, T., Iodi Carstens, M., Carstens, E.E., Pook, M.A., and Cortopassi, G.A. (2013). Frataxin deficiency leads to defects in expression of antioxidants and Nrf2 expression in dorsal root ganglia of the Friedrich's ataxia YG8R mouse model. Antioxid Redox Signal 19, 1481-1493.

(56) References Cited

OTHER PUBLICATIONS

Shen, M., Schmitt, S., Buac, D., and Dou, Q.P., Targeting the ubiquitin-proteasome system for cancer therapy, Expert opinion on therapeutic targets 17, 1091-1108, (2013).

Soucy, T.A., Smith, P.G., Milhollen, M.A., Berger, A.J., Gavin, J.M., Adhikari, S., Brownell, J.E., Burke, K.E., Cardin, D.P., Critchley, S. et al., An inhibitor of NEDD8-activating enzyme as a new approach to treat cancer, Nature 458, 732-736 (2009).

Trott, O. & Olson, A.J. AutoDock Vina: improving the speed and accuracy of docking with a new scoring function, efficient optimization, and multithreading. J Comput Chem 31, 455-461 (2010).

Tsou, A.Y., Friedman, L.S., Wilson, R.B. & Lynch, D.R., Pharmacotherapy for Friedreich ataxia, CNS Drugs 23, 213-223 (2009).

Vassilev, L.T., Vu, B.T., Graves, B., Carvajal, D., Podlaski, F., Filipovic, Z., Kong, N., Kammlott, U., Lukacs, C., Klein, C., et al., In vivo activation of the p53 pathway by small-molecule antagonists of MDM2, Science 303, 844-848 (2004).

Vaubel, R.A., and Isaya, G., Iron-sulfur cluster synthesis, iron homeostasis and oxidative stress in Friedreich ataxia, Mol Cell Neurosci 55, 50-61 (2013).

Weidemann, F., Stork, S., Liu, D., Hu, K., Herrmann, S., Ertl, G., and Niemann, M. (2013). Cardiomyopathy of Friedreich ataxia. J Neurochem 126 Suppl 1, 88-93.

Whitnall et al., "The MCK mouse heart model of Friedreich's ataxia: Alterations in iron-regulated proteins and cardiac hypertrophy are limited by iron chelation", Proceedings of the National Academy of Sciences, vol. 105, No. 28, Jul. 15, 2008, pp. 9757-9762.

Wright, G., Terada, K., Yano, M., Sergeev, I. & Mori, M. Oxidative, stress inhibits the mitochondrial import of preproteins and leads to their degradation, *Exp Cell Res* 263, 107-117 (2001).

Wu, L., Grigoryan, A.V., Li, Y., Hao, B., Pagano, M., and Cardozo, T.J., Specific small molecule inhibitors of Skp2-mediated p27 degradation, Chemistry & biology 19, 1515-1524 (2012).

Xu, P., et al. Quantitative proteomics reveals the function of unconventional ubiquitin chains in proteasomal degradation. Cell 137, 133-145 (2009).

Yandim, C., Natisvili, T., and Festenstein, R. (2013). Gene regulation and epigenetics in Friedreich's ataxia. J Neurochem 126 Suppl 1, 21-42.

Yang, Y., Ludwig, R.L., Jensen, J.P., Pierre, S.A., Medaglia, M.V., Davydov, I.V., Safiran, Y.J., Oberoi, P., Kenten, J.H., Phillips, A.C. et al. Small molecule inhibitors of HDM2 ubiquitin ligase activity stabilize and activate p53 in cells, Cancer cell 7, 547-559 (2005).

Yonashiro, R. et al., A novel mitochondrial ubiquitin ligase plays a critical role in mitochondrial dynamics, *EMBO J* 25, 3618-3626 (2006).

Yoon, T. & Cowan, J.A. Iron-sulfur cluster biosynthesis. Characterization of frataxin as an iron donor for assembly of [2Fe-2S] clusters in ISU-type proteins. J Am Chem Soc 125, 6078-6084 (2003).

Zaky, R.R et al., *Spectrochimica Acta Part A: Molecular and Biomolecular Spectroscopy*, 81, 28-34 (2011).

Zhang, W., and Sidhu, S.S., Development of inhibitors in the ubiquitination cascade, FEBS letters 588, 356-367 (2014).

Zyabrev et al., Zhurnal Organicheskoi Khimii, 30(5), 715-19; 1994.

Chatterjee et al., N-Methylation of Peptides and Proteins: An Important Element for Modulating Biological Functions; Angewandte Chemie 52 (1) (2013) 254-69.

Cherubini et al., "Src inhibitors modulate frataxin protein levels", Human Molecular Genetics, vol. 24. No. 15, May 6, 2015, pp. 4296-4305.

Dimmock et al. CAS: 107: 211450, 1987.

Hayashi, G.; Shen, Y.; Pedersen, T.L.; Newman, J. W; Pook, M.; Cortopassi, G. (2014) Hum Mo/ Genet, 23, 6838-47.

Hebert-Chatelain, E. (2013), Int J Biochem Cell Biol, 45, 90-98.

Hofer, A. and Wenz, T. (2014), Exp Gerontol, 56, 202-20.

Hunter, T. (2007), Mot Cell, 28, 730-38.

Puccio, H.; Anheim, M.; Tranchant, C. (2014), I, 170, 355-65.

Rai, M., et al., "HDAC Inhibitors Correct Frataxin Deficiency in a Friedreich Ataxia Mouse Model," PLoS ONE, vol. 3, No. 4, pp. 1-8, Apr. 2008.

Wells, J.A. (1990). Additivity of mutational effects in proteins. Biochemistry. 29(37):8509-8517.

| DRUG | FOLD INCREASE | SEM |
|---|---|---|
| FDA1 | 48,21 | 12,93 |
| FDA11 | 30,13 | 7,71 |
| FDA5 | 26,95 | 7,11 |
| FDA2 | 7,71 | 1,56 |
| FDA15 | 7,06 | 2,11 |
| FDA8 | 5,05 | 1,60 |
| FDA7 | 4,81 | 0,77 |
| FDA10 | 4,40 | 0,39 |
| FDA4 | 3,80 | 0,69 |
| FDA3 | 3,28 | 1,09 |
| FDA18 | 2,37 | 0,32 |
| FDA16 | 2,01 | 0,25 |
| FDA17 | 2,00 | 0,16 |
| FDA12 | 1,88 | 0,52 |
| FDA14 | 1,83 | 0,18 |
| FDA13 | 1,82 | 0,13 |
| FDA6 | 1,79 | 0,11 |
| FDA19 | 1,53 | 0,21 |
| FDA9 | 1,09 | 0,27 |

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
taatacgact cactataggg                                         20

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
ggggatccag catcttttcc ggaataggc                               29

METHODS FOR TREATING FRIEDREICH'S ATAXIA WITH ETRAVIRINE

CROSS REFERENCE

This application claims the benefit of U.S. Provisional Application No. 62/556,794, filed Sep. 11, 2017, the entire contents of which are incorporated herein by reference.

REFERENCE TO A "SEQUENCE LISTING" SUBMITTED AS ASCII TEXT FILES VIA EFS WEB

The Sequence Listing written in file 097459-1095723_000910US_SL.txt created on Nov. 9, 2018, 759 bytes, machine format IBM-PC, MS-Windows operating system, in accordance with 37 C.F.R. §§ 1.821 to 1.825, is hereby incorporated by reference in its entirety for all purposes.

TECHNICAL FIELD

The present invention relates generally to methods useful for the treatment of Friedreich's ataxia.

BACKGROUND OF THE INVENTION

Friedreich's ataxia (FRDA) is a progressive degenerative disease that affects mainly the muscular system, the nervous system, and the heart. With an estimated prevalence of 1 in 50.000 individuals in the Caucasian population, it is the most common form of inherited ataxia (Harding, 1981; Campuzano et al., 1996). Symptoms are progressive and generally appear during puberty, although the age of onset varies from childhood (2-3 years) to adulthood (after 25 years). Gait instability and lack of coordination are the main symptoms of the disease. Additional symptoms include dysarthria, areflexia, sensory loss, skeletal abnormalities, and left ventricular hypertrophy, which is the main cause of cardiac failure and premature death.

FRDA is caused by a homozygous hyperexpansion of GAA triplets (from about 70 to about 1000 triplets) within the first intron of the gene coding for frataxin (FXN) (Marmolino, 2011). This type of mutation reduces transcription of the FXN gene due to the formation of 'sticky' DNA structures and epigenetic changes, while maintaining a minimal residual amount of frataxin (about 10-30%), which is essential for survival during embryonic development. Frataxin is involved in several mitochondrial activities, such as iron metabolism and regulation of iron-sulfur clusters (ISCs) assembly, ATP generation, and oxidative stress control. Though frataxin is expressed ubiquitously in the organism (Campuzano et al., 1997), its deficiency primarily affects some regions of the central and peripheral nervous system, heart, skeleton, and endocrine pancreas, causing the main clinical and pathological features of the disease (Koeppen and Mazurkiewicz, 2013). Currently, there is no approved treatment for FRDA. There is a need for novel and effective treatments for FRDA.

BRIEF SUMMARY OF THE INVENTION

In one aspect, the invention features a method of treating Friedreich's ataxia in a subject in need thereof by administering to the subject a therapeutically effective amount of etravirine or a pharmaceutically acceptable salt thereof.

In another aspect, the invention features a method of increasing the expression of frataxin in a subject having Friedreich's ataxia by administering to the subject a therapeutically effective amount of etravirine or a pharmaceutically acceptable salt thereof.

In some embodiments of the above two aspects, the subject has a mutant FXN gene.

In another aspect, the invention features a method of treating a subject having a disease associated with the expression of a mutant FXN gene, comprising administering to the subject a therapeutically effective amount of etravirine or a pharmaceutically acceptable salt thereof. In some preferred embodiments, the subject has Friedreich's ataxia.

In some embodiments, the mutant FXN gene has a mutation in the first intron of the FXN gene. In some preferred embodiments, the mutation is a homozygous hyperexpansion of GAA.

In some embodiments of all aspects of the invention as described herein, the methods increase the expression of a precursor of frataxin, an intermediate form of frataxin, or a mature form of frataxin.

In some embodiments, the methods improve the subject's physical and cognitive performance. In some embodiments, the methods improve the subject's motor coordination, balance, or stability. In other embodiments, the methods prevent or alleviate vision impairment, hearing loss, or dysarthria associated with FRDA. In yet other embodiments, the methods prevent or alleviate skeletal or cardiac abnormalities associated with FRDA. In yet other embodiments, the methods increase the subject's survival.

In some embodiments, the methods described herein include administering to the subject one 100 mg to 300 mg tablet comprising etravirine twice daily, in which the subject is over 18 years of age and. In particular embodiments, the methods include administering to the subject one 200 mg tablet comprising etravirine twice daily.

In some embodiments, the methods described herein include administering to the subject two 50 mg to 150 mg tablets comprising etravirine twice daily, in which the subject is over 18 years of age and. In particular embodiments, the methods include administering to the subject two 100 mg tablets comprising etravirine twice daily.

In some embodiments, the methods described herein include administering to the subject one 100 mg tablet comprising etravirine twice daily, in which the subject is 6 years to less than 18 years of age and weighs greater than or equal to 16 kg to less than 20 kg.

In some embodiments, the methods described herein include administering to the subject one 125 mg tablet comprising etravirine twice daily, in which the subject is 6 years to less than 18 years of age and weighs greater than or equal to 20 kg to less than 25 kg.

In some embodiments, the methods described herein include administering to the subject one 150 mg tablet comprising etravirine twice daily, in which the subject is 6 years to less than 18 years of age and weighs greater than or equal to 25 kg to less than 30 kg.

In some embodiments, the methods described herein include administering to the subject one 200 mg tablet comprising etravirine twice daily, in which the subject is 6 years to less than 18 years of age and weighs greater than or equal to 30 kg.

In some embodiments of the methods described herein, the therapeutically effective amount of etravirine or a pharmaceutically acceptable salt thereof is administered to the subject after a meal.

In some embodiments of all aspects of the invention described herein, the subject is a mammal (e.g., a human).

BRIEF DESCRIPTION OF THE DRAWINGS

FIG. 2A again shows the western blot analysis of etravirine-treated FRDA lymphoblast cells, GM16203, with anti-frataxin (lower panel) and anti-tubulin (upper panel), as a loading control. Int: intermediate frataxin; mat: mature frataxin; tub: tubulin. FIG. 2B shows the relative mature frataxin levels measured by densitometric analysis of independent blots and normalized with tubulin levels. Data represent the average of three independent experiments±S.E.M. p-values were calculated with Student's t-test ($*p<0.05$; $**p<0.01$).

FIG. 3A provides representative blots for each of the seven FRDA lymphoblastoid cell lines after treatment with 300 nM etravirine for 24 h and western blot analysis with anti-frataxin and anti-tubulin, as a loading control.

FIG. 3B provides representative blots for the primary fibroblasts derived from two FRDA patients. Etr: etravirine; mat: mature frataxin; int: intermediate frataxin; tub: tubulin.

FIG. 5A shows the results of western blot analysis of cell extracts with anti-frataxin (lower panels) or anti-tubulin antibody (upper panels). FIG. 5B indicates the relative frataxin precursor levels, as measured by the western blots in FIG. 5A, when quantified as the densitometric ratio between frataxin precursor and tubulin for each lane. Data represent the mean from three different independent experiments. S.E.M: standard error of the mean.

FIGS. 6A (which duplicates FIG. 4A) and 6B show western blotting of lymphoblasts derived from an FRDA patient (GM16214) or from the unaffected carrier mother (GM16215), which were treated for 24 hrs (FIG. 6A) or 48 hrs (FIG. 6B) with 500 nM etravirine or vehicle alone. Etr: etravirine; mat: mature frataxin; tub: tubulin. A representative experiment, out of four showing similar results, is shown. FIGS. 6C and 6D show aconitase activity (340 nm) FRDA lymphoblastoid cell line GM16214 and lymphoblastoid cell line GM16215. Data represent the average of three (FIG. 6C) or five (FIG. 6D) independent experiments±S.E.M. p-values were calculated with Student's t-test ($*p<0.05$). FIG. 6E shows the cell viability results for GM16214 and GM16215 lymphoblasts, which were treated with 500 nM etravirine for 24 hrs (or with vehicle only) and then were treated with the indicated doses of $H_2O_2$ for 16 hrs. The graph shows loss of cell viability upon treatment with different doses of $H_2O_2$. One representative experiment, out of three performed with similar results, is shown.

DETAILED DESCRIPTION OF THE INVENTION

Figure 1A:
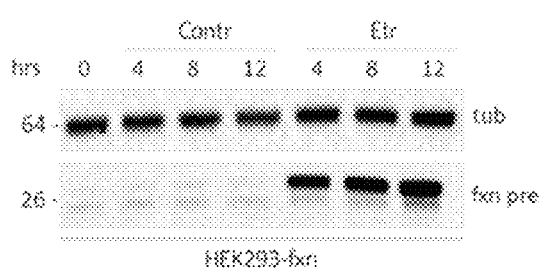
FIGS. 1A, 1B, and 1C show that etravirine promotes frataxin precursor accumulation in HEK 293 cells stably expressing frataxin (HEK293-fxn) (FIG. 1A), HEK 293 cells (FIG. 1B), and FRDA lymphoblast cells, GM16203 (FIG. 1C). Etr: etravirine; mat: mature frataxin; int: intermediate frataxin; and tub: tubulin. One out of three experiments performed for each cell line and giving similar results is shown.

The disclosure relates to methods for the treatment of Friedreich's ataxia (FRDA), an autosomal recessive ataxia caused by mutation of the FXN gene. In particular, the methods described herein includes administering to a subject having FRDA a therapeutically effective amount of etravirine, or a pharmaceutically acceptable salt thereof. Etravirine is demonstrated to increase the levels of frataxin precursor and intermediate and mature forms of frataxin.

I. Definitions

Unless otherwise stated, the following terms used in this application, including the specification and claims, have the definitions given below. Definition of standard chemistry terms may be found in reference works, including Carey and Sundberg (2007) "Advanced Organic Chemistry $5^{th}$ Ed." Vols. A and B, Springer Science+Business Media LLC, New York. The practice of the present invention will employ, unless otherwise indicated, conventional methods of synthetic organic chemistry, X-ray crystallography, protein NMR, mass spectroscopy, protein chemistry, biochemistry, preparative and analytical methods of chromatography, recombinant DNA techniques and pharmacology, within the skill of the art.

Any terms not directly defined herein shall be understood to have the meanings commonly associated with them as understood within the art of the invention. Certain terms are discussed herein to provide additional guidance to the practitioner in describing the compositions, devices, methods and the like of aspects of the invention, and how to make or use them. It will be appreciated that the same thing can be said in more than one way. Consequently, alternative language and synonyms can be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the invention herein.

All references included herein are incorporated by reference in their entirety, except that in cases of contradiction (e.g., different, inconsistent definitions of the same term), the instant specification takes priority.

The term "about" as used herein to modify a numerical value indicates a defined range around that value. If "X" were the value, "about X" would generally indicate a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X." When the quantity "X" only includes whole-integer values (e.g., "X carbons"), "about X" indicates the values X, X−1, and X+1.

When the term "about" is applied to the beginning of a numerical range, it applies to both ends of the range. Thus, "from about 5 to 20%" is equivalent to "from about 5% to about 20%." When "about" is applied to the first value of a set of values, it applies to all values in that set. Thus, "about 7, 9, or 11" is equivalent to "about 7, about 9, or about 11." However, when the modifier "about" is applied to describe only the end of a range or only a later value in a set of values, it applies only to that value or that end of the range. Thus, the range "about 2 to 10" is the same as "about 2 to about 10," but the range "2 to about 10" is not.

As used herein, the term "homozygous hyperexpansion of GAA" refers to a genetic mutation that causes FRDA in a subject. The subject has two mutated copies (e.g., homozygous) of the FXN gene and the mutated FXN gene has a hyperexpansion of GAA, which means that the triplet GAA repeats or expands from, e.g., about 70 to about 1000 triplets. In some embodiments, the hyperexpansion of GAA is within the first intron of the mutated FXN gene As used herein, the term "physical or cognitive performance" refers to a subject's ability to perform certain physical or mental tasks. Physical performance includes, e.g., the ability to walk, run, balance, and coordinate various muscles, and spatial awareness. Cognitive performance includes, e.g., logic reasoning, touch sensitivity, and hearing and vision acumen.

As used herein, the term "skeletal or cardiac abnormalities" refers to the abnormalities in a subject's skeletal system or heart that are caused by FRDA. Skeletal abnormalities associated with FRDA include, but are not limited to, inversion of the feet, a shortened foot with a high arch, and scoliosis. Cardiac abnormalities associated with FRDA include, but are not limited to, hypertrophic cardiomyopathy, an enlargement of cardiac muscles, and arrhythmia.

As used herein, the term "survival" refers to a length of time following the diagnosis of a disease or beginning or completing a particular course of therapy for a disease (e.g., FRDA).

As used herein, the terms "subject," "individual," and "patient" are used interchangeably herein to refer to a vertebrate, preferably a mammal, more preferably a human. Mammals include, but are not limited to, mice, murines, rats, simians, humans, farm animals, sport animals, and pets.

As used herein, the term "administering" includes oral administration, topical contact, administration as a suppository, intravenous, intraperitoneal, intramuscular, intralesional, intratumoral, intradermal, intralymphatic, intrathecal, intranasal, or subcutaneous administration to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The term "treating" refers to an approach for obtaining beneficial or desired results including, but not limited to, a therapeutic benefit or a prophylactic benefit. By therapeutic benefit is meant any therapeutically relevant improvement in FRDA.

As used herein, the term "therapeutically effective amount" refers to the amount of etravirine, or a pharmaceutically acceptable salt thereof, that is sufficient to effect beneficial or desired results (e.g., preventing or alleviating one or more symptoms associated with FRDA). The therapeutically effective amount may vary depending upon one or more of: severity and progression of FRDA, the weight and age of the subject, the manner of administration, the dosing regimen, whether etravirine is administered in combination with other compounds, and the like, which can readily be determined by one of ordinary skill in the art. For the purposes herein, a therapeutically effective amount is determined by such considerations as may be known in the art. The amount must be effective to achieve the desired therapeutic effect in a subject suffering from FRDA. The desired therapeutic effect may include, for example, prevention or amelioration of undesired symptoms associated with FRDA, or increasing the subject's survival.

As used herein, the term "pharmaceutically acceptable carrier" refers to a substance that aids the administration of an active agent to a cell, an organism, or a subject. "Pharmaceutically acceptable carrier" refers to a carrier or excipient that can be included in pharmaceutical compositions containing etravirine, or a pharmaceutically acceptable salt thereof, and that causes no significant adverse toxicological effect on the subject. Non-limiting examples of pharmaceutically acceptable carriers include water, NaCl, normal saline solutions, lactated Ringer's, normal sucrose, normal glucose, binders, fillers, disintegrants, lubricants, coatings, sweeteners, flavors and colors, liposomes, dispersion media, microcapsules, cationic lipid carriers, isotonic and absorption delaying agents, and the like. The carrier may also be substances for providing the formulation with stability, sterility, and isotonicity (e.g. antimicrobial preservatives, antioxidants, chelating agents, and buffers), for preventing the action of microorganisms (e.g., antimicrobial and antifungal agents, such as parabens, chlorobutanol, sorbic acid, and the like), or for providing the formulation with an edible flavor.

The linking term "comprising" or "comprise" as used herein is not closed. For example, "a composition comprising A" must include at least the component A, but it may also include one or more other components (e.g., B; B and C; B, C, and D; and the like).

As used herein, "or" should in general be construed non-exclusively. For example, an embodiment of "a composition comprising A or B" would typically present an aspect with a composition comprising both A and B. "Or" should, however, be construed to exclude those aspects presented that cannot be combined without contradiction (e.g., a composition pH that is between 9 and 10 or between 7 and 8).

"Pharmaceutically acceptable salt" refers to a salt of a compound of the invention which is made with counterions understood in the art to be generally acceptable for pharmaceutical uses and which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, morpholine, piperidine, dimethylamine, diethylamine and the like. Also included are salts of amino acids such as arginates and the like, and salts of organic acids like glucurmic or galactunoric acids and the like (see, e.g., Berge et al. (1977) *J. Pharm. Sci.*, 66, 1-19).

II. Library Screen

Friedreich's ataxia (FRDA) is an autosomal recessive ataxia caused by mutation of the FXN gene, which results in decreased frataxin expression, mitochondrial dysfunction, and oxidative stress. Currently, no treatment is available for FRDA patients. Traditional drug discovery approaches are usually very expensive and many years may be required for a candidate compound to reach market approval. Moreover, classical drug discovery processes are associated with a high risk of failure throughout the development phases. Drug repositioning is a method of finding a new indication for an existing and already approved drug and may serve as an opportunity for accelerating the discovery of new therapeutics, particularly in the field of orphan diseases, where resources are often limited (Sardana D, Zhu C, Zhang M, Gudivada R C, Yang L, Jegga A G. Drug repositioning for orphan diseases. Brief Bioinform 2011; 12(4):346-356). This type of approach has several advantages over the classic drug discovery, such as reduced development costs and shorter time to approval.

In FRDA, low levels of frataxin critically affect disease severity. Frataxin is synthesized in cytoplasmic ribosomes as a 210 kDa pre-protein precursor form and subsequently imported into mitochondria. In eukaryotes, the frataxin maturation process is mediated by the action of the MPP (Mitochondrial processing peptidase), which operates a sequential proteolysis by generating intermediate (21 kDa) and mature (14-17 kDa) frataxin forms. Since reduced amount of frataxin is the principal cause of the disease, increasing frataxin levels may serve as a therapeutic strategy to treat FRDA.

We pursued a drug repositioning approach to identify compounds that are able to increase frataxin levels and promote frataxin accumulation. Traditional drug discovery approaches are usually very expensive and many years may be required for a candidate compound to reach market approval. Moreover, classical drug discovery processes are associated with a high risk of failure, throughout the development phases. On the other hand, drug repositioning, which is finding a new indication for an existing and already approved drug, represents an opportunity for accelerating the discovery of new therapeutics and may represent a valuable strategy, particularly in the field of orphan diseases, where resources are often limited (Sardana D, Zhu C, Zhang M, Gudivada R C, Yang L, Jegga A G. Drug repositioning for orphan diseases. Brief Bioinform 2011; 12(4):346-356). This type of approach has several advantages over the classic drug discovery, such as reduced development costs and shorter time to approval. These advantages are due to the possibility of using existing pharmacokinetic, toxicology and safety data (Duraes F, Pinto M, Sousa E. Old Drugs as New Treatments for Neurodegenerative Diseases. Pharmaceuticals (Basel) 2018; 11(2); Shameer K, Readhead B, Dudley J T. Computational and experimental advances in drug repositioning for accelerated therapeutic stratification. Curr Top Med Chem 2015; 15(1):5-20).

Using a cell-based reporter assay to monitor variation in frataxin amount, we performed a high-throughput screening of a library containing 853 FDA-approved drugs. From the screening, we isolated 19 compounds that promote frataxin accumulation. These drugs belong to different pharmacological classes and have various molecular targets. Upon validation of the individual drugs, we confirmed that almost all of the identified hits were indeed able to increase frataxin levels in different cellular systems. In the subsequent validation steps, considering the life-long nature of FRDA, we prioritized candidate drugs that are known to be tolerated in a chronic treatment regimen. In particular, we focused our attention on etravirine, an anti-retroviral drug currently used for the treatment of HIV.

Etravirine is a non-nucleoside reverse transcriptase inhibitor (NNRTI) of human immunodeficiency virus type 1 (HIV-1) that has been approved (TN INTELENCE®) for the treatment of HIV-1 infectin since 2008 (Usach I, Melis V, Penis J E. Non-nucleoside reverse transcriptase inhibitors: a review on pharmacokinetics, pharmacodynamics, safety and tolerability. J Int AIDS Soc 2013; 16:1-14). Etravirine blocks the RNA-dependent and DNA-dependent DNA polymerase activities by binding directly to reverse transcriptase (RT) in two conformationally distinct modes (Das K, Clark A D, Jr., Lewi P J, et al. Roles of conformational and positional adaptability in structure-based design of TMC125-R165335 (etravirine) and related non-nucleoside reverse transcriptase inhibitors that are highly potent and effective against wild-type and drug-resistant HIV-1 variants. Journal of medicinal chemistry 2004; 47(10):2550-2560). This binding causes a disruption of the enzyme's catalytic site, resulting in inhibition of the enzyme activity. (Guillemont J, Pasquier E, Palandjian P, et al. Synthesis of novel diarylpyrimidine analogues and their antiviral activity against human immunodeficiency virus type 1. Journal of medicinal chemistry 2005; 48(6):2072-2079). Etravirine is currently prescribed as a treatment for HIV-positive patients. Etravirine is safe and well tolerated over a long-term regimen and is currently prescribed as a life-long treatment, starting from as young as six years of age.

Etravirine is also able to promote frataxin accumulation in cells derived from FRDA patients and restore physiological frataxin levels comparable to that of a healthy control. Importantly, etravirine treatment does not show any toxic effect and does not affect cell viability.

II. Methods of Treatment

The disclosure provides methods of treating FRDA by administering to a subject a therapeutically effective amount of etravirine or a pharmaceutically acceptable salt thereof. As described herein, etravirine is demonstrated to increase the expression of a precursor of frataxin, an intermediate form of frataxin, or a mature form of frataxin. Increasing frataxin levels in a subject may reduce or alleviate one or more symptoms of FRDA and improve the subject's physical or cognitive performance (e.g., the ability to walk, run, balance, and coordinate various muscles, spatial awareness, logic reasoning, touch, hearing, and vision sensitivity). Administering to a subject a therapeutically effective amount of etravirine or a pharmaceutically acceptable salt thereof may improve the subject's motor coordination, balance, or stability, and prevent or alleviate vision impairment, hearing loss, or dysarthria. In some embodiments, administering to a subject a therapeutically effective amount of etravirine or a pharmaceutically acceptable salt thereof may also prevent or alleviate skeletal or cardiac abnormalities associated with FRDA (e.g., inversion of the feet, a shortened foot with a high arch, scoliosis, hypertrophic cardiomyopathy, an enlargement of cardiac muscles, and arrhythmia).

In some embodiments, the subject has a mutant FXN gene. In particular embodiments, the mutant FXN gene may include a mutation in the first intron of the FXN gene (e.g., a homozygous hyperexpansion of GAA).

In some aspects, the invention presents the use of etravirine in a method of any of the aspects or embodiments disclosed herein. In some aspects, the invention presents the use of etravirine in the manufacture of a medicament for use in a method of any of the aspects and embodiments disclosed herein.

III. Pharmaceutical Compositions

Etravirine can be used as pharmaceutical compositions, together with one or more pharmaceutically acceptable excipients or vehicles. Such excipients include, for example, liquids such as water, saline, glycerol, polyethyleneglycol, hyaluronic acid, ethanol, cyclodextrins, and modified cyclodextrins (i.e., sufobutyl ether cyclodextrins). Suitable excipients for non-liquid formulations are also known to those of skill in the art. Pharmaceutically acceptable salts can be used in pharmaceutical compositions containing etravirine and include, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients and salts is available in *Remington's Pharmaceutical Sciences*, 18th Edition (Easton, Pa.: Mack Publishing Company, 1990). The pharmaceutical compositions may also include isomers, tautomers, or racemic or non-racemic mixtures of isomers of etravirine.

Additionally, auxiliary substances, such as wetting or emulsifying agents, biological buffering substances, surfactants, and the like, may be present. A biological buffer can be virtually any solution which is pharmacologically acceptable and which provides the formulation with the desired pH, e.g., a pH in the physiologically acceptable range. Examples of buffer solutions include, e.g., saline, phosphate buffered saline, Tris buffered saline, Hank's buffered saline, and the like.

Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of etravirine in combination with a pharmaceutically acceptable carrier and, in addition, may include other pharmaceutical agents, adjuvants, diluents, buffers, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., etravieine and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents, tonicifying agents, and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, referenced above.

For oral administration, the composition will generally take the form of a tablet, capsule, a soft-gel capsule, or may be an aqueous or non-aqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, etravirine may be combined with emulsifying and suspending agents. If desired, flavoring, coloring or sweetening agents may be added as well. Other optional components for incorporation into an oral formulation herein include, but are not limited to, preservatives, suspending agents, thickening agents, and the like.

IV. Routes of Administration and Dosage

A pharmaceutically or therapeutically effective amount of etravirine will be delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. Thus, in some embodiments, the effective amount for a given situation may be determined by routine experimentation.

Pharmaceutical compositions that include etravirine, or a pharmaceutically acceptable salt thereof, may be formulated for, e.g., intravenous administration, parenteral administration, subcutaneous administration, intramuscular administration, intra-arterial administration, intrathecal administration, or intraperitoneal administration. The pharmaceutical composition may also be formulated for, or administered via, oral, nasal, spray, aerosol, rectal, or vaginal administration. In particular embodiments, pharmaceutical compositions containing etravirine, or a pharmaceutically acceptable salt thereof, may be formulated as a tablet for oral administration. For injectable formulations, various effective pharmaceutical carriers are known in the art. See, e.g., Remington: The Science and Practice of Pharmacy, 22th ed., (2012) and ASHP Handbook on Injectable Drugs, 18th ed., (2014).

The dosage of the pharmaceutical compositions depends on factors including the route of administration, the severity or stage of FRDA, and physical characteristics, e.g., age, weight, sex, or general health of the subject. Typically, the amount of the pharmaceutical composition contained within a single dose or multiple doses may be an amount that effectively prevents, delays, or treats FRDA without inducing significant toxicity. A pharmaceutical composition may include a dosage of etravirine, or a pharmaceutically acceptable salt thereof, ranging from 0.01 to 500 mg/kg (e.g., 0.01, 0.05, 0.1, 0.2, 0.3, 0.4, 0.5, 0.6, 0.7, 0.8, 0.9, 1, 1.25, 1.5, 1.75, 2, 2.5, 3, 3.5, 4, 4.5, 5, 6, 7, 8, 9, 10, 12.5, 15, 17.5, 20, 25, 30, 35, 40, 45, 50, 55, 60, 65, 70, 75, 80, 85, 90, 95, 100, 125, 150, 175, 200, 225, 250, 300, 350, 400, 450, or 500 mg/kg) and, in a more specific embodiment, about 0.1 to about 50 mg/kg (e.g., 0.1, 0.2, 0.3, 0.4, 0.5, 0.6, 0.7, 0.8, 0.9, 1, 1.1, 1.2, 1.25, 1.3, 1.4, 1.5, 1.6, 1.7, 1.75, 1.8, 1.9, 2, 2.25, 2.5, 2.75, 3, 3.25, 3.5, 3.75, 4, 4.5, 5, 6, 7, 8, 9, 10, 12.5, 15, 17.5, 20, 25, 30, 35, 40, 45, or 50 mg/kg) and, in a more specific embodiment, about 1 to about 10 mg/kg (e.g., 1, 1.1, 1.2, 1.25, 1.3, 1.4, 1.5, 1.6, 1.7, 1.75, 1.8, 1.9, 2, 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, 9.75, or 10 mg/kg). The dosage may be adapted by the physician in accordance with conventional factors, such as the extent of FRDA and different parameters of the subject (e.g., age, weight, sex, or medical conditions than may slow or speed drug metabolism). The subject may be administered as many doses as is required to reduce or alleviate the signs and symptoms of FRDA.

The pharmaceutical compositions are administered in a manner compatible with the dosage formulation and in such amount as is therapeutically effective to result in an improvement or remediation of the symptoms of FRDA (e.g., an improvement gait stability, motor coordination, or general physical performance). The pharmaceutical compositions are administered in a variety of dosage forms, e.g., intravenous dosage forms, subcutaneous dosage forms, and oral dosage forms (e.g., ingestible solutions, drug release capsules). In particular embodiments, the pharmaceutical compositions are administered in oral dosage forms. The pharmaceutical composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, preparations suitable for iontophoretic delivery, or aerosols. The compositions may be formulated according to conventional pharmaceutical practice. Pharmaceutical compositions may be administered to a subject in need thereof, for example, one or more times (e.g., 1, 2, 3, 4, 5, 6, 7, 8, 9, 10, or more times) daily, weekly, monthly, biannually, annually, or as medically necessary. Dosages may be provided in either single- or multiple-dose regimens.

In some embodiments, the pharmaceutical compositions containing etravirine, or a pharmaceutically acceptable salt thereof, may be in tablet form for oral administration (e.g., INTELENCE®). Depending on the age of the patient, the dosage and frequency for administering tablet forms of etravirine, or a pharmaceutically acceptable salt thereof, may vary. For example, in some embodiments, adult patients may be administered one 100 mg to 300 mg tablet (e.g., one 100 mg tablet, one 150 mg tablet, one 200 mg tablet, one 250 mg tablet, or one 300 mg tablet) twice a day. In some embodiments, adult patients may be administered two 50 mg to 150 mg tablets (e.g., two 50 mg tablets, two 75 mg tablets, two 100 mg tablets, two 125 mg tablets, or two 150 mg tablets) twice a day. In particular embodiments, the tablets may be administered after a meal. For pediatric patients, e.g., patients 6 years to less than 18 years of age and weighting at least 16 kg, the dosage and frequency of administration may depend on the weight of the patient and may follow the recommendations listed in Table 1 below.

TABLE 1

| Weight (kg) | Dose |
|---|---|
| greater than or equal to 16 kg to less than 20 kg | 100 mg twice daily |
| greater than or equal to 20 kg to less than 25 kg | 125 mg twice daily |
| greater than or equal to 25 kg to less than 30 kg | 150 mg twice daily |
| greater than or equal to 30 kg | 200 mg twice daily |

In some aspects, the invention presents a method as set forth herein, further comprising administering to the subject one or more agents selected from the group consisting of an interferon and a ubiquitin-competing molecule. In some aspects, the agent is an interferon. In some aspects, the interferon is gamma interferon, for example, using a method as set forth in U.S. Pat. No. 8,815,230.

In some aspects, the invention presents a method as set forth herein, further comprising administering to the subject an Src inhibitor, for example, as set forth in U.S. patent application Ser. No. 15/630,328 (U.S. Pat. App. Pub. No. 2017/0296540 A1).

EXAMPLES

Example 1—Library Screening and Effects of Etravirine

Screening and Cell-Based Assay

The FDA-approved drug library (SELLECKCHEM SCREENING LIBRARIES®) that was used in the screening was composed of 853 drugs. The library was provided in a total of ten 96-well plate, with the drugs at a stock concentration of 10 mM in dimethyl sulfoxide (DMSO). To evaluate the effect of drugs on frataxin abundance, we generated a fusion construct between frataxin and ProLabel that was used as a reporter in a cell-based assay. The system is based on 3-galactosidase enzyme fragment complementation (Eglen, 2002). The 6 kDa ProLabel tag encodes the inactive a fragment of the β-galactosidase enzyme. When the Ω subunit of the enzyme is added, together with the substrate, the two subunits combine to form an active enzyme that generates a chemiluminescent signal, the intensity of which correlates to the amount of frataxin-ProLabel fusion present in the cells. To validate this system, cells transfected with frataxin ProLabel were treated with the proteasome inhibitor MG132. By blocking the proteasome-dependent degradation of all cellular proteins, the MG132 allows the accumulation of frataxin (Rufini A, Fortuni S, Arcuri G, et al.

Preventing the ubiquitin-proteasome-dependent degradation of frataxin, the protein defective in Friedreich's ataxia. Hum Mol Genet 2011; 20(7):1253-1261). Indeed, treatment of frataxin-ProLabel transfected cells with MG132 promotes frataxin accumulation, which results in a 5-fold increase in the intensity of the luminescence signal. This system allows us to evaluate subtle variations in frataxin levels in a sensitive and accurate manner.

For the screening, HEK-293 cells were transiently transfected with pCMV-fxn-ProLabel. 24 hours after transfection, cells were plated in a 96-well at a concentration of $5 \times 10^4$ cells per well. 24 hours after re-plating, cells were treated with an individual drug per well, at a final concentration of 10 μM. DMSO treatment was used as negative control, while MG132-treated cells were included in each plate and considered as internal positive control. After 24 hours, the complementary β-galactosidase subunit and the substrate were added and chemiluminescence emission was measured by luminometer reading. Specifically, the ProLabel enzyme fragment complementation assay was performed using the PATHHUNTER® ProLabel Detection Kit (Discoverx), according to the manufacturer's instructions. The chemiluminescent signal was monitored over a period of 210 minutes. Six technical replicates were performed for each of the ten 96-well plate of the library.

To analyse the FDA-approved drug screening results, an arbitrary threshold was established for each plate as the average of the luminescence measured in all the wells of the plate plus 2 standard deviations. Luminescence signal from each well was then normalized on threshold value. Drugs giving a fold increase greater than or equal to 1 in at least four out of six replicates were considered positive hits.

Cell Culture and Transfection Conditions

Lymphoblastoid cell lines from one healthy subject [GM16215] and 7 FRDA patients [GM16228, GM16203, GM16214, GM16223, GM16210, GM16205, GM16216], and primary fibroblasts from 2 FRDA patients [GM02816 and GM04078], were obtained from NIGMS Human Genetic Cell Repository, Coriell Institute for Medical Research (Camden, N.J., USA). Lymphoblasts and fibroblasts were grown at 37° C. and 5% $CO_2$ and were respectively cultured in RPMI or DMEM, supplemented with 15% FBS, 100 U/mg penicillin/streptomycin and 2 mM L-glutamine.

Human embryonic kidney HEK-293 cells were grown in Dulbecco's modified Eagle's medium (DMEM) supplemented with 10% fetal bovine serum (FBS), 100 U/mg penicillin/streptomycin and 2 mM L-glutamine at 37° C. and 5% $CO_2$. Transfections were performed using Lipofectamine 2000 method (Invitrogen, Carlsbad, USA), according to the manufacturer's instructions.

HEK-293 Flp-In cells (Invitrogen) are HEK-293 variants having a stable and isogenic integration and expression of a transfected gene, as previously described by Condò et al., 2007. Condò I et al., Hum Mol Genet 2007; 16(13):1534-1540. Cells were maintained in DMEM supplemented with 10% FBS and the antibiotics penicillin/streptomycin 100 U/mg and L-glutamine 2 mM.

cDNA Expression Constructs

The pIRES2-fxn$^{1-210}$ construct contains human frataxin cDNA cloned into pIRES2-EGFP (Clontech) bicistronic expression vector and was previously generated in our laboratory (Condò et al. 2006). pCMV-fxn-ProLabel construct was generated by subcloning PCR using the primers 5'-TAATACGACTCACTATAGGG-3' (SEQ ID NO: 1) (T7) and 5'-GGGGATCCAGCATCTTTT CCGGAATAGGC-3' (SEQ ID NO: 2) (BamH1, no stop) to amplify frataxin cDNA from the plasmid pIRES2-fxn$^{1-210}$. Frataxin cDNA was then inserted between HindIII and BamHI restriction sites of the expression vector pCMV-ProLabel-C1. The HA-Ub construct was generated as described in Treier M., Staszewski L. M., Bohmann D. Ubiquitin-dependent c-Jun degradation in vivo is mediated by the delta domain. Cell. 1994; 78:787-798.

Drug Treatment

For the validation steps, etravirine (TMC125) was purchased from Selleckchem and was dissolved in DMSO at a stock concentration of 10 mM. HEK-293 Flp-In cells, stably overexpressing frataxin, were treated with the drug (or only DMSO) for 24 hours at final concentration of 10 μM. FRDA cells were treated with different concentration of etravirine. For all drug (and no drug) treatments, the final concentration of DMSO in the cell culture medium was 0.1%.

Cell Lysates and Western Blot Analysis

Total cell extracts were prepared in lysis buffer (50 mM Tris-HCl, pH 7.5, 150 mM NaCl, 1% Igepal CA-630, 5 mM EDTA, 5 mM EGTA) supplemented with complete protease inhibitor cocktail (Roche Diagnostics, Indianapolis, Ind., USA). Lysates were clarified by centrifugation and supernatants were mixed with 4× Laemmli sample buffer (50 mM Tris pH 6.8, 2% SDS, 10% gliycerol, 0.0025% bromophenol blue, 5% beta-mercaptoethanol), boiled for 5 min, resolved by precast 12% SDS-PAGE gels (Bio-Rad Laboratories, Hercules, Calif., USA) and transferred to 0.2 μM nitrocellulose membrane (TRANS-BLOT® TURBO™ Transfer pack, Bio-Rad). Membranes were blocked with 5% non-fat dry milk, 0.1% Tween 20 in phosphate-buffered saline (PBS) and incubated with the indicated primary and secondary antibodies. The immunoreactive bands were detected by ECL (GE Healthcare, Chalfont St. Giles, UK) and imaged with a ChemiDoc XRS system (Bio-Rad). Densitometry analysis was performed using the ImageLab 4.1 Software (Bio-Rad). To analyse the western blot densitometry results, a Student's t test was applied. All values are expressed as means±1 S.E.M.

Antibodies

The following antibodies were used for western blot analysis: monoclonal (mAb) anti-frataxin (clone 18A5DB1, Abcam, Cambridge, UK), mAb anti-α-tubulin (clone DM1A, Sigma-Aldrich), and secondary antibody horseradish peroxidase (HRP)-conjugated goat anti-mouse (Thermo Fisher Scientific, Waltham, Mass., USA).

Results

Etravirine Promotes Accumulation of Frataxin Precursor

Figure 1B:
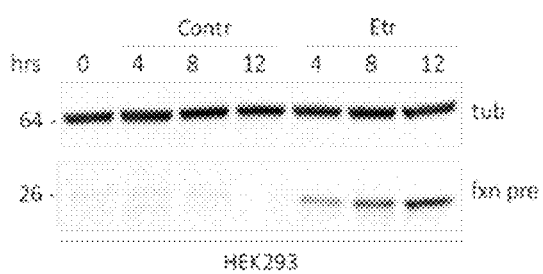
Figure 1C:
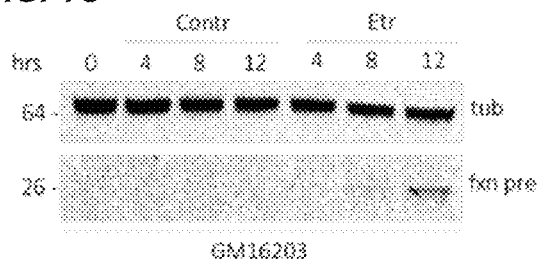

The identified candidate drugs were individually validated for their ability to promote frataxin accumulation in different cell types. Among the different drugs, we focused our attention on etravirine, a non-nucleoside reverse transcriptase inhibitor (NNRT), currently used as a therapeutic for HIV. We initially tested etravirine on three different cell lines as shown in FIGS. 1A-1C. Protein extracts from the cell lines were resolved on SDS-PAGE and analyzed by western blot with anti-frataxin antibody and anti-tubulin as a loading control. We tested etravirine on HEK293 Flp-In stably transfected with frataxin (HEK293-fxn) at 10 which is the concentration used in the screening. As shown in FIG. 1A, etravirine treatment promotes a rapid and robust increase in the amount of frataxin precursor already detectable after 4 hours of treatment and even higher after 12 hours. Moreover, frataxin precursor accumulation can also be detected in HEK293 expressing only endogenous frataxin (FIG. 1B), and most importantly, also in lymphoblastoid cells derived from FRDA patients (FIG. 1C).

Figure 1D:
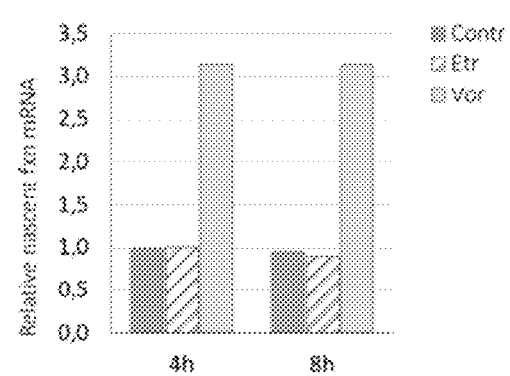
FIG. 1D shows the nascent frataxin transcripts levels of HEK 293-fxn stably expressing frataxin after the cells had been treated with 10 μM etravirine, 10 μM vorinostat, or DMSO for 4 or 8 hours. Etr: etravirine; Vor: vorinostat.
Figure 1E:
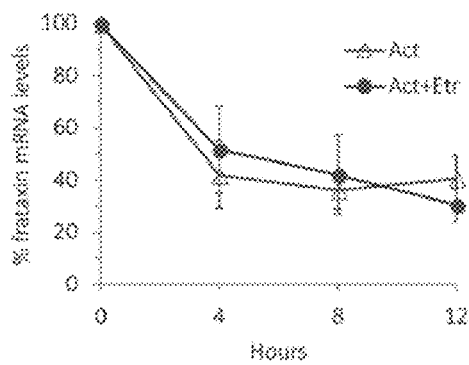
FIG. 1E provides real-time PCR results showing the relative levels of total frataxin mRNA for HEK 293-fxn stably expressing frataxin that were treated with 100 nM actinomycin D (open triangles) or 100 nM actinomycin D plus 10 μM etravirine (solid circles) for the indicated times. The graph shows the average of three independent experiments±S.E.M.

We then investigated whether the observed increase in frataxin protein levels is due to an upregulation of the frataxin mRNA, either promoted by an increase in the translation rate of frataxin mRNA or by its stabilization. To understand whether etravirine promotes de novo synthesis of frataxin mRNA, we metabolically labeled nascent transcripts through the incorporation of 5-ethynyl uridine (EU). Through a click chemistry-based reaction, biotin was then conjugated to EU-labelled transcripts, thus allowing selective isolation and analysis of newly synthesized mRNA. We therefore quantitatively analyzed the relative amount of newly synthesized frataxin mRNA in etravirine-treated HEK293-fxn cells, compared to untreated control cells. As shown in FIG. 1D, we did not observe any difference in the relative amount of newly synthesized frataxin mRNA in etravirine-treated HEK293-fxn cells, compared to untreated control cells, while, as expected, the HDAC inhibitor Vorinostat, which was used as a positive control, significantly upregulates frataxin mRNA synthesis. We then analyzed the effect of etravirine on the decay of frataxin transcript observed upon treatment with actinomycin. HEK293-fxn cells were treated with actinomycin for 4, 8 or 12 hours in the presence or absence of etravirine and frataxin mRNA was quantitated by RT-PCR. As shown in FIG. 1E, the half-life of frataxin mRNA is not affected by etravirine, indicating that etravirine does not promote a stabilization of the frataxin transcript. These data suggest that etravirine might be able to enhance the translation efficiency of frataxin mRNA, thus resulting in increased amount of frataxin protein.

FIGS. 1A to 1E show that etravirine promotes frataxin precursor accumulation in different cell types. HEK 293-fxn stably expressing frataxin (A), HEK 293 (B), or FRDA lymphoblast cell line GM16203 (C) were treated with 10 μM etravirine for the indicated time points. Protein extracts were resolved on SDS-PAGE and analyzed by western blot with anti-frataxin antibody and anti-tubulin as a loading control. Etr: etravirine; tub: tubulin; fxn pre: frataxin precursor. One out of three experiments performed for each cell line and giving similar results is shown. D) HEK 293-fxn stably expressing frataxin were treated with 10 μM Etravirine, 10 μM Vorinostat or DMSO for 4 or 8 hours. Quantitative analysis of newly-synthesized FXN mRNA was performed by metabolic labeling of nascent RNA using the Click-iT Nascent RNA Capture Kit (Life Technologies), followed by biotin conjugation and isolation with streptavidin beads, according to provider instructions. Nascent frataxin transcripts levels were quantitated by real-time PCR relative to the expression of the control genes ACTB, GUSB and ATP5J. Etr: etravirine; Vor: vorinostat. E) HEK 293-fxn stably expressing frataxin were treated with 100 nM Actinomycin D (open triangles) or 100 nM Actinomycin D plus 10 μM Etravirine (solid circles) for the indicated times. Relative levels of total frataxin mRNA were measured by real-time PCR and normalized on expression levels of three control genes ATP5J, GUSB and ACTB using the ΔΔCt method. The graph shows the average of three independent experiments±S.E.M. %.

Etravirine Induces Dose-Dependent Increase in Mature Frataxin

In order to evaluate whether the precursor that readily accumulates upon etravirine treatment can be converted into the mature functional form of frataxin, we tested the effect of different doses of etravirine, ranging from 100 nM to 10 μM, on a lymphoblastoid cell line, GM16203, derived from an FRDA patient. The cells were treated with the indicated doses of etravirine for 24 hours. Cell extracts were resolved on SDS-PAGE and analyzed by western blot analysis with anti-frataxin and anti-tubulin, as a loading control. We tested different doses, ranging from 100 nM to 3 μM, on the lymphoblastoid cell line GM16203. We observed that, while at 10 etravirine mostly induces precursor accumulation, but doses as low as 300 nM are sufficient to promote a significant increase in the intermediate and mature frataxin forms (FIGS. 2A and 2B).

Figure 2A:
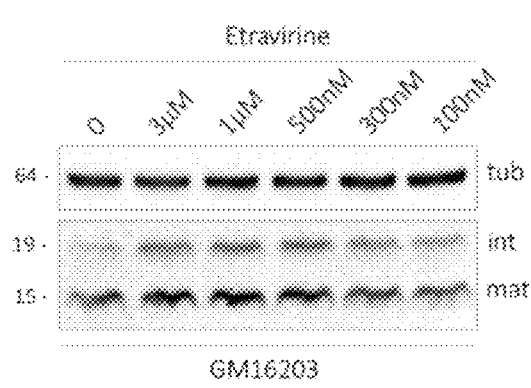
FIGS. 2A and 2B show that etravirine promotes a dose-dependent increase in mature frataxin levels.
Figure 2B:
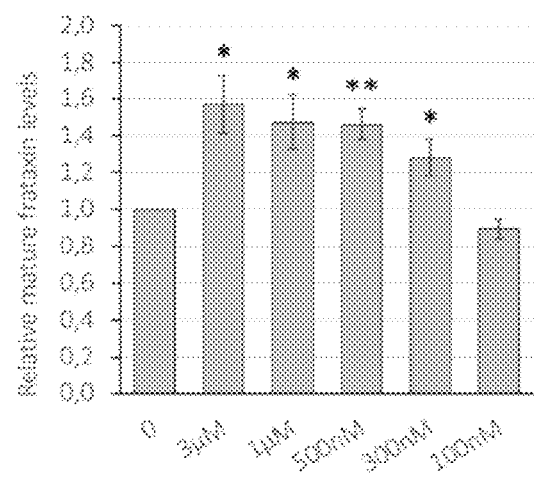

FIGS. 2A and 2B show that etravirine promotes dose-dependent increase in mature frataxin levels. A) FRDA lymphoblast cells, GM16203, were treated with the indicated doses of etravirine for 24 hours. Cell extracts were resolved on SDS-PAGE and analyzed by western blot analysis with anti-frataxin (lower panel) and anti-tubulin (upper panel), as a loading control. Int: intermediate frataxin; mat: mature frataxin; tub: tubulin. B) The graph represents the relative mature frataxin levels measured by densitometric analysis of independent blots and normalized with tubulin levels. Data represent the average of three independent experiments±S.E.M. p-values were calculated with Student's t-test (*$p<0.05$; **$p<0.01$)

Etravirine Efficacy in FRDA Cells

Figure 3A:
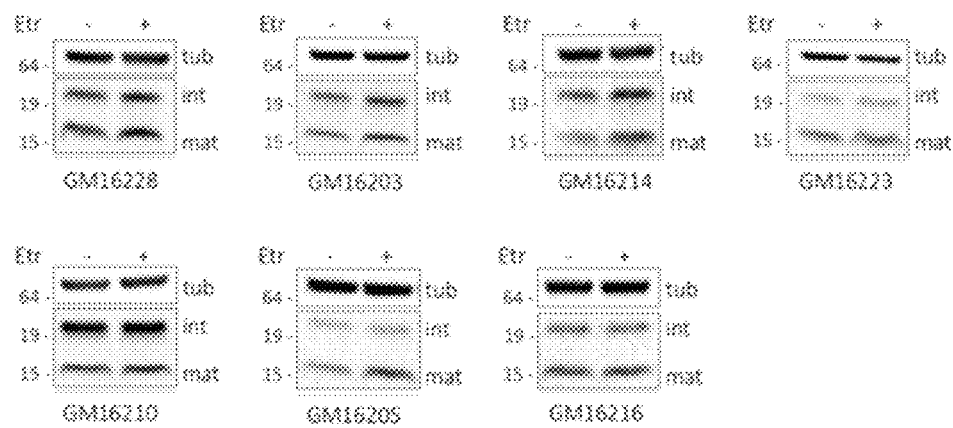
FIG. 3A shows that etravirine increases mature frataxin levels in seven FRDA lymphoblastoid cell lines. Etr: etravirine; mat: mature frataxin; int: intermediate frataxin; and tub: tubulin.
Figure 3B:
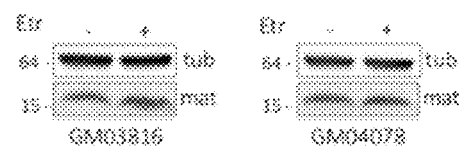
FIG. 3B shows that etravirine increases mature frataxin levels in primary FRDA fibroblasts derived from two FRDA patients. Etr: etravirine; mat: mature frataxin; int: intermediate frataxin; and tub: tubulin.
Figure 3C:
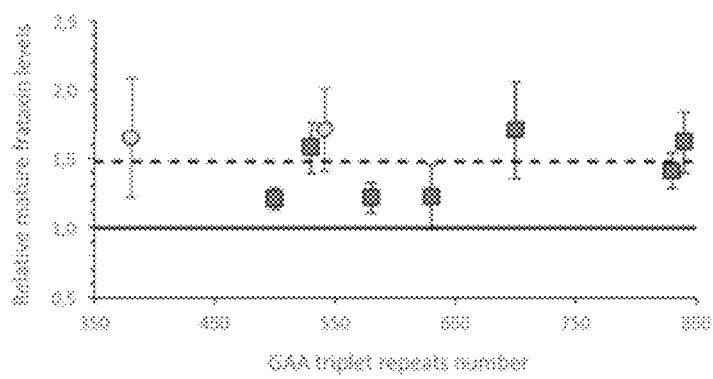
FIG. 3C shows the average fold increase in mature frataxin levels observed for the FRDA lymphoblastoid cell lines (dark grey squares) and the primary FRDA fibroblast (light grey circles) upon etravirine treatment. The X-axis shows the size of the mutated allele. Densitometry analysis was performed on mature frataxin levels and normalized with tubulin levels. Data represents the results from three independent experiments for each cell line±S.E.M. The solid line represents the average mature frataxin levels in untreated control cells and dashed line represents the average mature frataxin levels in etravirine treated cells.
Figure 4A:
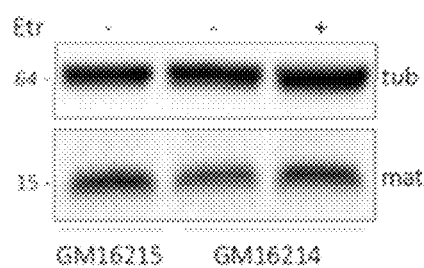
FIG. 4A shows etravirine restores physiological frataxin levels in FRDA patients cell line, GM16214, compared to the frataxin levels in an unaffected carrier sibling cell line, GM 16215.
Figure 4B:
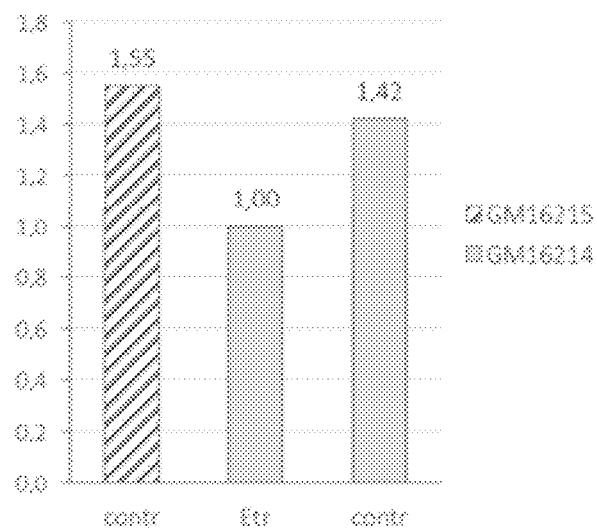
FIG. 4B shows the mature frataxin levels normalized with tubulin levels as measured by densitometry of the western blots in FIG. 4A.

We chose the minimal effective dose (300 nM) to evaluate the efficacy of etravirine over a broad range of cells derived from FRDA patients. In particular, we analysed 7 lymphoblastoid cell lines derived from FRDA patients and primary fibroblasts derived from two different FRDA patients. Each cell line was treated with 300 nM etravirine for 24 hours. Cell extracts were resolved on SDS-PAGE and analyzed by western blot analysis with anti-frataxin and anti-tubulin, as a loading control. Etravirine promotes increase in intermediate and mature frataxin levels in all the cell lines tested upon 24 hours of treatment (FIGS. 3A-3B). The average fold increase in mature frataxin levels promoted by etravirine treatment is reported in FIG. 3C for each lymphoblastoid cell line and fibroblasts tested. Overall, etravirine was able to promote a 50% increase in mature frataxin levels in cells derived from FRDA patients. Moreover, the graph in FIG. 3C indicates that there is no significant correlation between the GAA triplet repeats number on the longer allele and the ability to upregulate frataxin in response to etravirine. Table 2 below also shows the average fold increase of frataxin levels in different cell lines.

TABLE 2

| FRDA cells | Cell Line ID | GAA repeats | Average | SEM |
| --- | --- | --- | --- | --- |
| Lymphoblasts | GM16228 | 840 | 1.62 | 0.22 |
| | GM16203 | 830 | 1.41 | 0.13 |
| | GM16214 | 700 | 1.71 | 0.35 |
| | GM16223 | 630 | 1.22 | 0.23 |
| | GM16210 | 580 | 1.22 | 0.11 |
| | GM16205 | 530 | 1.58 | 0.19 |
| | GM16216 | 500 | 1.21 | 0.08 |
| Fibroblasts | GM03816 | 380 | 1.65 | 0.43 |
| | GM04078 | 541 | 1.71 | 0.30 |

In order to prove that the increase in frataxin levels could be relevant for the purpose of restoring the physiological conditions, frataxin levels in etravirine treated FRDA cells were compared to the levels observed in cells derived from unaffected carrier sibling. FRDA lymphoblasotid cell line, GM16214, and lymphoblastoid cell line, GM16215, derived from unaffected carrier sibling were treated for 24 hours with 300 nM etravirine. Cell extracts were resolved on SDS-PAGE and analyzed by western blot with anti-frataxin antibody and anti-tubulin as a loading control. Indeed, FIG.

4 shows that frataxin accumulation in treated patients cells is comparable to frataxin levels in untreated cells derived from healthy control, suggesting that frataxin accumulation promoted by etravirine treatment is therapeutically significant.

REFERENCES

Campuzano V, Montermini L, Lutz Y, Cova L, Hindelang C, Jiralerspong S, Trottier Y, Kish S J, Faucheux B, Trouillas P, Authier F J, Durr A, Mandel J L, Vescovi A, Pandolfo M, Koenig M. 1997. Frataxin is reduced in Friedreich ataxia patients and is associated with mitochondrial membranes. Hum Mol Genet 6:1771-1780.

Campuzano V, Montermini L, Molto M D, Pianese L, Cossee M, Cavalcanti F, Monros E, Rodius F, Duclos F, Monticelli A, al. e. 1996. Friedreich's ataxia: autosomal recessive disease caused by an intronic GAA triplet repeat expansion. Science 271:1423-1427.

de Bethune M P. 2010. Non-nucleoside reverse transcriptase inhibitors (NNRTIs), their discovery, development, and use in the treatment of HIV-1 infection: a review of the last 20 years (1989-2009). Antiviral Res 85:75-90.

Eglen R M. 2002. Enzyme fragment complementation: a flexible high throughput screening assay technology. Assay Drug Dev Technol 1:97-104.

Harding A E. 1981. Friedreich's ataxia: a clinical and genetic study of 90 families with an analysis of early diagnostic criteria and intrafamilial clustering of clinical features. Brain 104:589-620.

Koeppen A H, Mazurkiewicz J E. 2013. Friedreich ataxia: neuropathology revised. J Neuropathol Exp Neurol 72:78-90.

Marmolino D. 2011. Friedreich's ataxia: past, present and future. Brain Res Rev 67:311-330.

Rufini A, Cavallo F, Condo I, Fortuni S, De Martino G, Incani O, Di Venere A, Benini M, Massaro D S, Arcuri G, Serio D, Malisan F, Testi R. 2015. Highly specific ubiquitin-competing molecules effectively promote frataxin accumulation and partially rescue the aconitase defect in Friedreich ataxia cells. Neurobiol Dis 75:91-99.

Rufini A, Fortuni S, Arcuri G, Condo I, Serio D, Incani O, Malisan F, Ventura N, Testi R. 2011. Preventing the ubiquitin-proteasome-dependent degradation of frataxin, the protein defective in Friedreich's ataxia. Hum Mol Genet 20:1253-1261.

Sardana D, Zhu C, Zhang M, Gudivada R C, Yang L, Jegga A G. 2011. Drug repositioning for orphan diseases. Brief Bioinform 12:346-356.

Shameer K, Readhead B, Dudley J T. 2015. Computational and experimental advances in drug repositioning for accelerated therapeutic stratification. Curr Top Med Chem 15:5-20.

Soragni E, Miao W, Iudicello M, Jacoby D, De Mercanti S, Clerico M, Longo F, Piga A, Ku S, Campau E, Du J, Penalver P, Rai M, Madara J C, Nazor K, O'Connor M, Maximov A, Loring J F, Pandolfo M, Durelli L, Gottesfeld J M, Rusche J R. 2014. Epigenetic therapy for Friedreich ataxia. Ann Neurol 76:489-508.

Usach I, Melis V, Penis J E. 2013. Non-nucleoside reverse transcriptase inhibitors: a review on pharmacokinetics, pharmacodynamics, safety and tolerability. J Int AIDS Soc 16:1-14.

Example 2—Additional Results from Library Screening and Effects of Etravirine

Etravirine can promote a significant increase in frataxin levels in cells derived from FRDA patients, without showing any toxic effect. Importantly, frataxin accumulation in treated patient cell lines is comparable to frataxin levels in unaffected carrier cells suggesting that etravirine could be therapeutically relevant. Indeed, etravirine treatment restores the activity of the iron-sulphur cluster containing enzyme aconitase and confers resistance to oxidative stress in cells derived from FRDA patients.

Additional Methods

Cell Viability Assay

Cells were treated with etravirine 500 nM for 24 h, then transferred (40000 cells/100 ul/well) into 96-well tissue culture plates. Cultures were supplemented for 16 h with 12.5 µM, 25 µM and 50 µM $H_2O_2$ (Sigma-Aldrich). After $H_2O_2$ treatment, 1 mg/ml XTT (2,3-Bis-(2-Methoxy-4-Nitro-5-Sulfophenyl)-2H-Tetrazolium-5-Carboxanilide) (INVITROGEN™, Thermo Fisher Scientific, Waltham, Mass. USA) and 0.25% Phenazine methosulfate (PMS, Fisher Scientific, Thermo Fisher Scientific, Waltham, Mass. USA) were added (25 µL/well) and cells were incubated for additional 2 h. Results were expressed as the percentage of reduction of absorbance at 450 nm by calibration with the absorbance of the control (untreated) cells.

Evaluation of Aconitase Activity

Whole-cell extracts from GM16215 lymphoblasts, GM16214 lymphoblasts and GM16214 lymphoblasts treated with etravirine were prepared in ice-cold CelLytic M buffer (Sigma-Aldrich) supplemented with 2 mM sodium citrate and Complete EDTA-free protease inhibitor cocktail (Roche Diagnostic). Spectrophotometric aconitase assays were performed at 25° C. with 100 µg of cell extracts using the BIOXYTECH Aconitase-340™ Assay (OxisResearch™ 21041). Spectrophotometric citrate synthase activities were assessed at 25° C. with 10-20 µg of cell extracts using the Citrate Synthase Assay Kit (Sigma-Aldrich CS0720). Aconitase activities were referred to the specific activity of citrate synthase to correct for mitochondrial content. For the calculation of the activities, one unit of enzyme was expressed as the amount of protein that converted 1 µmol of substrate per minute at 25° C. Quantitative data are presented as mean±SEM of at least three independent experiments.

Additional Results

FDA-Approved Drug Library High-Throughput Screening

As discussed in Example 1, in order to identify drugs that increase frataxin levels, we performed a high-throughput screening of a library containing 853 FDA-approved drugs. From the screening, we isolated 19 candidate drugs, potentially involved in the regulation of frataxin levels, which were selected for further analysis.

Figures 5A, 5B:
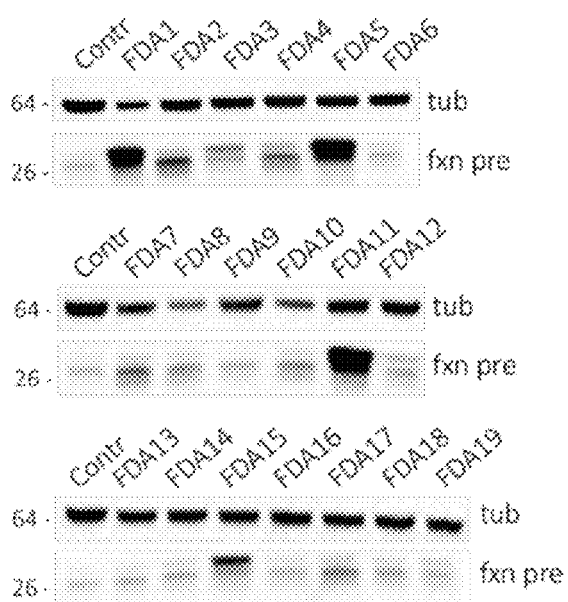
FIGS. 5A and 5B further show the results of validation of the candidate drugs.

The identified candidate drugs were individually validated for their ability to promote frataxin accumulation. We initially tested the selected compounds on HEK293 Flp-In cells stably transfected with frataxin (HEK293-fxn) at 10 µM, which is the concentration used in the screening. This cell line contains a single copy of frataxin cDNA integrated into the genome and therefore, with relatively low levels of overexpression, enables the detection of all frataxin forms. As shown in FIGS. 5A and 5B, 13 out of the 19 selected drugs were indeed able to promote at least a 2-fold increase in frataxin precursor levels. Frataxin precursor appears as a doublet in western blot analysis, however the exact nature of these two forms has never been thoroughly investigated. Most of the selected drugs are able to upregulate one of the two bands or both. Notably, three of the selected candidates (FDA1, FDA11 and FDA5) promote a striking upregulation of frataxin precursor (FIGS. 5A and 5B). Among these three drugs, we selected etravirine (FDA11), a non-nucleoside reverse transcriptase inhibitor (NNRT), currently used as a therapeutic for HIV-1 infection. This drug was chosen for further investigation taking into account its minimal impact on cell viability and its potential to be used in a chronic therapy without important side effects.

FIGS. 5A and 5B further show details of the candidate drugs' validation as per the procedure of Example 1. A) HEK 293-fxn were treated with 10 µM of each candidate drug for 24 h. Cell extracts were resolved on SDS-PAGE and analyzed by western blot analysis with anti-fraxatin (lower panels) or anti tubulin antibody (upper panels) B) The table indicates the relative frataxin precursor levels, as measured by the western blot in A), quantified as the densitometric ratio between frataxin precursor and tubulin for each lane. Data represent the mean from three different independent experiments. S.E.M: standard error of the mean.

Etravirine can Functionally Rescue Frataxin Deficiency in FRDA Cells

Figure 6A:
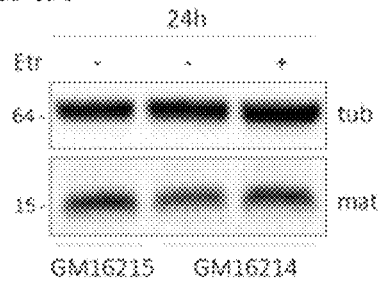
FIGS. 6A to 6E show that etravirine functionally rescues frataxin deficiency in FRDA patient cells.
Figure 6B:
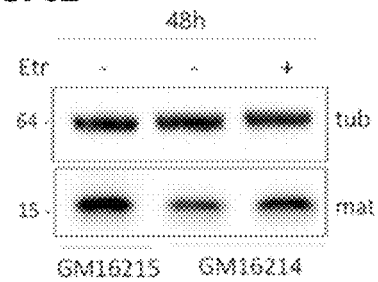

As previously discussed in Example 1, in order to prove that the increase in frataxin levels could be relevant for the purpose of restoring the physiological conditions, frataxin levels in etravirine-treated FRDA cells were compared to the levels observed in cells derived from the unaffected carrier mother after 24 and 48 hours. As shown again in FIGS. 6A-B, frataxin levels in FRDA cells increase over time during etravirine treatment and compare nicely to levels in unaffected carrier cells. These data suggest that frataxin accumulation promoted by etravirine treatment could be therapeutically significant.

Figure 6C:
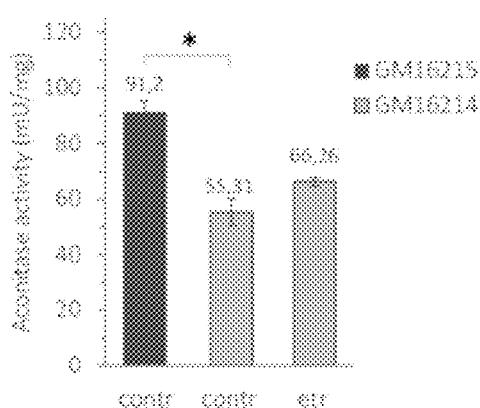
Figure 6D:
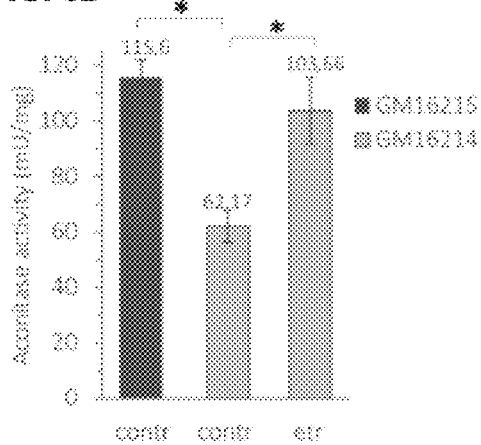

To further explore the therapeutic potential of etravirine, we considered its ability to correct some of the defects associated with frataxin loss in cells derived from patients. Frataxin participates to the biogenesis of iron-sulphur clusters (ISC) in the cells, thus frataxin deficiency is associated with a deficit in the activity of many ISC-containing enzymes, such as aconitase. To evaluate whether the increase in frataxin levels promoted by etravirine treatment is sufficient to restore ISC biogenesis in FRDA patient-derived cells, we measured the activity of aconitase upon etravirine treatment and compared it to the activity observed in cells derived from the healthy carrier mother. As shown in FIGS. 6C-6D, etravirine is able to restore aconitase activity in FRDA cells after 48 hours.

Figure 6E:
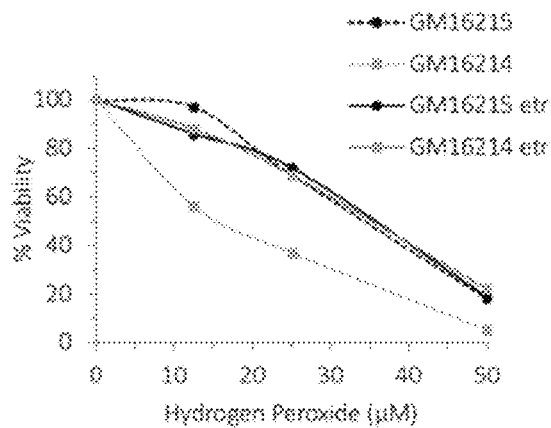

Importantly, cells derived from FRDA patients have an impaired anti-oxidant response and show increased sensitivity to oxidative stress-induced cell death (Schulz J B, Dehmer T, Schols L, et al. Neurology 2000; 55(11):1719-1721; Chantrel-Groussard K, Geromel V, Puccio H, et al. Hum Mol Genet 2001; 10(19):2061-2067). We therefore tested whether, by promoting frataxin accumulation, etravirine can revert this phenotype and confer resistance to hydrogen peroxide-mediated stress. We measured the loss of cell viability induced by different doses of hydrogen peroxide we observed that etravirine treatment significantly protects lymphoblastoid patient cells from $H_2O_2$-induced cell death (FIG. 6E). Indeed, cell viability in etravirine-treated patient cells is comparable to what observed in cells derived from the heterozygous healthy mother. Importantly, no further improvement in cell viability is observed in healthy control cells upon etravirine treatment.

These data indicate that etravirine treatment can significantly correct functional defects induced by frataxin deficiency in FRDA patient-derived cells.

FIGS. 6A to 6E show how etravirine functionally can rescue frataxin deficiency in FRDA patient cells. FRDA lymphoblastoid cell line GM16214 and lymphoblastoid cell line GM16215 derived from the unaffected carrier mother were treated for 24 hrs (A) or 48 hrs (B) with 500 nM etravirine or vehicle alone. Cell extracts were resolved on SDS-PAGE and analysed by western blot with anti-frataxin antibody and anti-tubulin as a loading control. Etr: etravirine; mat: mature frataxin; tub: tubulin. A representative experiment, out of four showing similar results, is shown. C-D) FRDA lymphoblasotid cell line GM16214 was cultured in the presence of 500 nM etravirine (etr) or vehicle only (contr) for 24 hrs (A) or 48 hrs (B). Lymphoblastoid cell line GM16215 derived from the unaffected carrier mother was cultured in the presence of vehicle only (contr). Aconitase activity was measured spectrophotometrically at 340 nm as described in the Methods section. Data represent the average of three (C) or five (D) independent experiments±S.E.M. p-values were calculated with Student's t-test (*p<0.05) E): Lymphoblasts derived from FRDA patient (GM16214) or from the unaffected carrier mother (GM16215), were either treated with 500 nM etravirine for 24 hrs or with vehicle only. Cells were then treated with the indicated doses of $H_2O_2$ for 16 hrs. The graph shows loss of cell viability upon treatment with different doses of $H_2O_2$. Cell viability was measured by the XTT assay as described in the Methods section. One representative experiment, out of three performed with similar results, is shown.

Discussion

The antiviral drug etravirine is able to promote frataxin accumulation in cells derived from FRDA patients, restoring the physiological frataxin levels. Importantly, etravirine treatment does not show any toxic effect on frataxin-deficient cells and does not affect cell viability at any of the tested doses. Notably, etravirine does not affect the rate of neo-synthesis of frataxin mRNA nor it impacts on the half-life of frataxin transcript, suggesting the involvement of a translational mechanism that leads to frataxin protein accumulation upon etravirine treatment. These observations are consistent with the screening method that we adopted to select the candidate drugs. Indeed, the frataxin-reporter fusion that we used for the screening is transiently transfected and expressed from a cDNA under the constitutively active CMV promoter. Moreover, since the GAA repeats are located within an intronic region of the frataxin locus, they are not present in the cDNA. Drugs that increase the levels of the frataxin-reporter fusion are therefore not expected to regulate the frataxin endogenous promoter and to act through a GAA repeats-independent mechanism. Indeed, etravirine is able to promote frataxin accumulation in different cell types, both in transfected cells expressing frataxin from an exogenous construct as well as in primary or immortalized cells derived from FRDA patients, containing GAA repeats expansion. Importantly, we did not observe any correlation between the efficacy of etravirine and the presence or the length of the GAA repeats.

Without intending to be limited by theory, etravirine might function by enhancing the rate of translation of frataxin mRNA or by preventing the degradation of frataxin protein. However, when etravirine's effect was compared to the effect of the general proteasome inhibitor MG132, which is known to prevent the degradation of frataxin precursor (e.g., Rufini et al. 2011) and to increase its levels, we observed that etravirine-induced frataxin accumulation is strikingly stronger than what observed upon MG132 treatment, suggesting that de novo protein synthesis is taking place upon etravirine treatment and accounts for the massive and rapid accumulation of frataxin precursor.

Frataxin deficient cells have an inefficient mitochondrial metabolism, which leads to increased generation of ROS, coupled with impaired ability to rise an adequate antioxidant response. These features make FRDA patients cells particularly susceptible to oxidative stress (Chantrel-Groussard et al. 2001; Bradley J L, Homayoun S, Hart P E, Schapira A H, Cooper J M. Role of oxidative damage in Friedreich's ataxia. Neurochem Res 2004; 29(3):561-567). Importantly, frataxin accumulated upon etravirine treatment could be functionally relevant, in that it can correct some of the pathogenic consequences of frataxin deficiency in cells derived from FRDA patients, such as deficiency in ISC-containing enzymes activity and increased sensitivity to oxidative stress. In conclusion, the well characterized safety profile (Allavena C, Katlama C, Cotte L, et al. Long-term efficacy and safety of etravirine-containing regimens in a real-life cohort of treatment-experienced HIV-1-infected patients. Infect Dis (Lond) 2016; 48(5):392-398) and very low toxicity induced by etravirine, make this drug a promising candidate for Friedreich ataxia therapy.

In some aspects, the invention presents various aspects and embodiments for illustration; it is not intended to be exhaustive or to limit the invention to the precise forms disclosed. Persons skilled in the relevant art can appreciate that many modifications and variations are possible in light of the above teachings. It should be noted that the language used in the specification has been principally selected for readability and instructional purposes, and it may not have been selected to delineate or circumscribe the inventive subject matter. Accordingly, the disclosure of the aspects of the invention is intended to be illustrative, but not limiting, of the scope of the invention.

All references, issued patents, and patent applications cited within the body of the specification are hereby incorporated by reference in their entirety, for all purposes except insofar as their disclosure contradicts the express disclosure herein.

ADDITIONAL REFERENCES

1. Campuzano V, Montermini L, Molto M D, et al. Friedreich's ataxia: autosomal recessive disease caused by an intronic GAA triplet repeat expansion. Science (New York, N.Y. 1996; 271(5254):1423-1427.
2. Harding A E. Friedreich's ataxia: a clinical and genetic study of 90 families with an analysis of early diagnostic criteria and intrafamilial clustering of clinical features. Brain 1981; 104(3):589-620.
3. Mateo I, Llorca J, Volpini V, Corral J, Berciano J, Combarros O. GAA expansion size and age at onset of Friedreich's ataxia. Neurology 2003; 61(2):274-275.
4. Durr A, Cossee M, Agid Y, et al. Clinical and genetic abnormalities in patients with Friedreich's ataxia. N Engl J Med 1996; 335(16):1169-1175.
5. Parkinson M H, Boesch S, Nachbauer W, Mariotti C, Giunti P. Clinical features of Friedreich's ataxia: classical and atypical phenotypes. J Neurochem 2013; 126 Suppl 1:103-117.
6. Koeppen A H, Ramirez R L, Becker A B, et al. The pathogenesis of cardiomyopathy in Friedreich ataxia. PLoS One 2015; 10(3):e0116396.
7. Campuzano V, Montermini L, Lutz Y, et al. Frataxin is reduced in Friedreich ataxia patients and is associated with mitochondrial membranes. Hum Mol Genet 1997; 6(11):1771-1780.
8. Marmolino D. Friedreich's ataxia: past, present and future. Brain Res Rev 2011; 67(1-2):311-330.
9. De Biase I, Chutake Y K, Rindler P M, Bidichandani S I. Epigenetic silencing in Friedreich ataxia is associated with depletion of CTCF (CCCTC-binding factor) and antisense transcription. PLoS One 2009; 4(11):e7914.
10. Filla A, De Michele G, Cavalcanti F, et al. The relationship between trinucleotide (GAA) repeat length and clinical features in Friedreich ataxia. Am J Hum Genet 1996; 59(3):554-560.
11. Condò I, Ventura N, Malisan F, Rufini A, Tomassini B, Testi R. In vivo maturation of human frataxin. Hum Mol Genet 2007; 16(13):1534-1540.
12. Gonzalez-Cabo P, Palau F. Mitochondrial pathophysiology in Friedreich's ataxia. J Neurochem 2013; 126 Suppl 1:53-64.
13. Koeppen A H, Morral J A, Davis A N, et al. The dorsal root ganglion in Friedreich's ataxia. Acta Neuropathol 2009; 118(6):763-776.
14. Koeppen A H, Becker A B, Qian J, Feustel P J. Friedreich Ataxia: Hypoplasia of Spinal Cord and Dorsal Root Ganglia. J Neuropathol Exp Neurol 2017; 76(2):101-108.
15. Pastore A, Puccio H. Frataxin: a protein in search for a function. J Neurochem 2013; 126 Suppl 1:43-52.
16. Koeppen A H, Mazurkiewicz J E. Friedreich ataxia: neuropathology revised. J Neuropathol Exp Neurol 2013; 72(2):78-90.
17. Strawser C, Schadt K, Hauser L, et al. Pharmacological therapeutics in Friedreich ataxia: the present state. Expert review of neurotherapeutics 2017; 17(9):895-907.
18. Tai G, Corben L A, Yiu E M, Milne S C, Delatycki M B. Progress in the treatment of Friedreich ataxia. Neurol Neurochir Pol 2018; 52(2):129-139.
19. Tomassini B, Arcuri G, Fortuni S, et al. Interferon gamma upregulates frataxin and corrects the functional deficits in a Friedreich ataxia model. Hum Mol Genet 2012; 21(13):2855-2861.
20. Sandeo S, Scott B D, McMackin M Z, et al. Dyclonine rescues frataxin deficiency in animal models and buccal cells of patients with Friedreich's ataxia. Hum Mol Genet 2014; 23(25):6848-6862.
21. Santoro A, Anjomani Virmouni S, Paradies E, et al. Effect of diazoxide on Friedreich ataxia models. Hum Mol Genet 2018; 27(6):992-1001.
22. Libri V, Yandim C, Athanasopoulos S, et al. Epigenetic and neurological effects and safety of high-dose nicotinamide in patients with Friedreich's ataxia: an exploratory, open-label, dose-escalation study. Lancet 2014.
23. Chutake Y K, Lam C C, Costello W N, Anderson M P, Bidichandani S I. Reversal of epigenetic promoter silencing in Friedreich ataxia by a class I histone deacetylase inhibitor. Nucleic Acids Res 2016; 44(11):5095-5104.
24. Codazzi F, Hu A, Rai M, et al. Friedreich ataxia-induced pluripotent stem cell-derived neurons show a cellular phenotype that is corrected by a benzamide HDAC inhibitor. Hum Mol Genet 2016; 25(22):4847-4855.
25. Soragni E, Gottesfeld J M. Translating HDAC inhibitors in Friedreich's ataxia. Expert Opin Orphan Drugs 2016; 4(9):961-970.
26. Rufini A, Cavallo F, Condo I, et al. Highly specific ubiquitin-competing molecules effectively promote frataxin accumulation and partially rescue the aconitase defect in Friedreich ataxia cells. Neurobiol Dis 2015; 75:91-99.
27. Li L, Shen X, Liu Z, et al. Activation of Frataxin Protein Expression by Antisense Oligonucleotides Targeting the Mutant Expanded Repeat. Nucleic Acid Ther 2018; 28(1): 23-33.
28. Katlama C, Clotet B, Mills A, et al. Efficacy and safety of etravirine at week 96 in treatment-experienced HIV 28. type-1-infected patients in the DUET-1 and DUET-2 trials. Antivir Ther 2010; 15(7):1045-1052.
29. Nelson M, Hill A, van Delft Y, Moecklinghoff C. Etravirine as a Switching Option for Patients with HIV RNA Suppression: A Review of Recent Trials. AIDS Res Treat 2014; 2014:636584.
30. Eglen R M. Enzyme fragment complementation: a flexible high throughput screening assay technology. Assay and drug development technologies 2002; 1(1 Pt 1):97-104.
31. Benini M, Fortuni S, Condo I, et al. E3 Ligase RNF126 Directly Ubiquitinates Frataxin, Promoting Its Degradation: Identification of a Potential Therapeutic Target for Friedreich Ataxia. Cell Rep 2017; 18(8):2007-2017.
32. Rufini A, Fortuni S, Arcuri G, et al. Preventing the ubiquitin-proteasome-dependent degradation of frataxin, the protein defective in Friedreich's ataxia. Hum Mol Genet 2011; 20(7):1253-1261.
33. Ye H, Rouault T A. Human iron-sulfur cluster assembly, cellular iron homeostasis, and disease. Biochemistry 2010; 49(24):4945-4956.
34. Rotig A, de Lonlay P, Chretien D, et al. Aconitase and mitochondrial iron-sulphur protein deficiency in Friedreich ataxia. Nat Genet 1997; 17(2):215-217.
35. Bradley J L, Blake J C, Chamberlain S, Thomas P K, Cooper J M, Schapira A H. Clinical, biochemical and molecular genetic correlations in Friedreich's ataxia. Hum Mol Genet 2000; 9(2):275-282.
36. Condo I, Malisan F, Guccini I, Serio D, Rufini A, Testi R. Molecular control of the cytosolic aconitase/IRP1 switch by extramitochondrial frataxin. Hum Mol Genet 2010; 19(7):1221-1229.
37. Schulz J B, Dehmer T, Schols L, et al. Oxidative stress in patients with Friedreich ataxia. Neurology 2000; 55(11):1719-1721.
38. Chantrel-Groussard K, Geromel V, Puccio H, et al. Disabled early recruitment of antioxidant defenses in Friedreich's ataxia. Hum Mol Genet 2001; 10(19):2061-2067.
39. Paupe V, Dassa E P, Goncalves S, et al. Impaired nuclear Nrf2 translocation undermines the oxidative stress response in Friedreich ataxia. PLoS One 2009; 4(1): e4253.
40. Sardana D, Zhu C, Zhang M, Gudivada R C, Yang L, Jegga A G. Drug repositioning for orphan diseases. Brief Bioinform 2011; 12(4):346-356.
41. Duraes F, Pinto M, Sousa E. Old Drugs as New Treatments for Neurodegenerative Diseases. Pharmaceuticals (Basel) 2018; 11(2).
42. Shameer K, Readhead B, Dudley J T. Computational and experimental advances in drug repositioning for accelerated therapeutic stratification. Curr Top Med Chem 2015; 15(1):5-20.
43. Usach I, Melis V, Penis J E. Non-nucleoside reverse transcriptase inhibitors: a review on pharmacokinetics, pharmacodynamics, safety and tolerability. J Int AIDS Soc 2013; 16:1-14.
44. Das K, Clark A D, Jr., Lewi P J, et al. Roles of conformational and positional adaptability in structure-based design of TMC125-R165335 (etravirine) and related non-nucleoside reverse transcriptase inhibitors that are highly potent and effective against wild-type and drug-resistant HIV-1 variants. Journal of medicinal chemistry 2004; 47(10):2550-2560.
45. Guillemont J, Pasquier E, Palandjian P, et al. Synthesis of novel diarylpyrimidine analogues and their antiviral activity against human immunodeficiency virus type 1. Journal of medicinal chemistry 2005; 48(6):2072-2079.
46. de Bethune M P. Non-nucleoside reverse transcriptase inhibitors (NNRTIs), their discovery, development, and use in the treatment of HIV-1 infection: a review of the last 20 years (1989-2009). Antiviral Res 2010; 85(1):75-90.
47. Bradley J L, Homayoun S, Hart P E, Schapira A H, Cooper J M. Role of oxidative damage in Friedreich's ataxia. Neurochem Res 2004; 29(3):561-567.
48. Allavena C, Katlama C, Cotte L, et al. Long-term efficacy and safety of etravirine-containing regimens in a real-life cohort of treatment-experienced HIV-1-infected patients. Infect Dis (Lond) 2016; 48(5):392-398.

What is claimed is:

1. A method of treating Friedreich's ataxia in a subject in need thereof, comprising administering to the subject a therapeutically effective amount of etravirine or a pharmaceutically acceptable salt thereof.

2. The method of claim 1, wherein the method improves the subject's physical or cognitive performance.

3. The method of claim 2, wherein the method improves the subject's motor coordination, balance, or stability.

4. The method of claim 2, wherein the method prevents or alleviates vision impairment, hearing loss, or dysarthria associated with FRDA Friedreich's ataxia.

5. The method of claim 2, wherein the method prevents or alleviates skeletal or cardiac abnormalities associated with FRDA Friedreich's ataxia.

6. The method of claim 1, wherein the method increases the subject's survival.

7. The method of claim 1, wherein the method comprises administering to the subject one 100 mg to 300 mg tablet comprising etravirine twice daily and wherein the subject is over 18 years of age.

8. The method of claim 7, wherein the method comprises administering to the subject one 200 mg tablet comprising etravirine twice daily.

9. The method of claim 1, wherein the method comprises administering to the subject two 50 mg to 150 mg tablets comprising etravirine twice daily and wherein the subject is over 18 years of age.

10. The method of claim 9, wherein the method comprises administering to the subject two 100 mg tablets comprising etravirine twice daily.

11. The method of claim 1, wherein the method comprises administering to the subject one 100 mg tablet comprising etravirine twice daily and wherein the subject is 6 years to less than 18 years of age and weighs greater than or equal to 16 kg to less than 20 kg.

12. The method of claim 1, wherein the method comprises administering to the subject one 125 mg tablet comprising etravirine twice daily and wherein the subject is 6 years to less than 18 years of age and weighs greater than or equal to 20 kg to less than 25 kg.

13. The method of claim 1, wherein the method comprises administering to the subject one 150 mg tablet comprising etravirine twice daily and wherein the subject is 6 years to less than 18 years of age and weighs greater than or equal to 25 kg to less than 30 kg.

14. The method of claim 1, wherein the method comprises administering to the subject one 200 mg tablet comprising etravirine twice daily and wherein the subject is 6 years to less than 18 years of age and weighs greater than or equal to 30 kg.

15. The method of claim 1, wherein the therapeutically effective amount of etravirine, or a pharmaceutically acceptable salt thereof, is administered to the subject after a meal.

16. The method of claim 1, wherein the subject is a mammal.

17. The method of claim 16, wherein the mammal is a human.

* * * * *